(12) United States Patent
Leffler et al.

(10) Patent No.: US 7,700,763 B2
(45) Date of Patent: Apr. 20, 2010

(54) 3-TRIAZOLYL-GALACTOSIDE INHIBITORS OF GALECTINS

(75) Inventors: Hakon Leffler, Lund (SE); Bader Abdalraheem Bader Salameh, Manchester (GB); Ulf Nilsson, Lind (SE)

(73) Assignee: Forskarpatent I Syd AB, Lund (SE)

( * ) Notice: Subject to any disclaimer, the term of this patent is extended or adjusted under 35 U.S.C. 154(b) by 40 days.

(21) Appl. No.: 11/561,465

(22) Filed: Nov. 20, 2006

(65) Prior Publication Data

US 2007/0185041 A1    Aug. 9, 2007

Related U.S. Application Data

(63) Continuation of application No. PCT/SE2005/000766, filed on May 23, 2005.

(30) Foreign Application Priority Data

May 21, 2004    (SE)    ................................ 0401301

(51) Int. Cl.
  *C07H 5/04*    (2006.01)
  *A61K 31/7052*    (2006.01)
(52) U.S. Cl. ................. 536/55; 536/54; 536/123.13; 514/23; 514/53
(58) Field of Classification Search ............. 536/55, 536/54, 123.13; 514/23, 53
  See application file for complete search history.

(56) References Cited

U.S. PATENT DOCUMENTS

2002/0044932 A1 *  4/2002  Liu et al. ................. 424/143.1

2006/0148712 A1 *  7/2006  Liu et al. ................. 514/13

FOREIGN PATENT DOCUMENTS

| EP | 0561523 | 9/1993 |
| WO | 0007624 | 2/2000 |
| WO | 02057284 A1 | 7/2002 |

OTHER PUBLICATIONS

Roy et al. Abstracts of Papers, 226th ACS National Meeting, New York, NY, United States, Sep. 7-11, 2003, CARB-027.*
Tornoe et al. J. Org. Chem., 2002, 67, p. 3057-3064.*
Marco-Contelles et al. Tetrahedron, 1999, 55, p. 10511-10526.*
Sorme et al., "Low Micromolar Inhibitors of Galectin-3 Based on 3'-Derivatization of N-Acetyllactosamine"; ChemBioChem 2002, vol. 3, Weinheim, Germany; pp. 183-189.
Kiran et al., "Thermodynamic analysis of the binding of galactose and poly-N-acetyllactosamine derivatives to human galectin-3"; FEBS letters, 2001, vol. 500; pp. 75-79.
Helland et al., "Methyl 3-amino-3-deoxy-B-D-galactopyranosyl-(1-4)-2-acetamido-2-deoxy-B-D-glucopyranoside: an inhibitor of UDP-D-galactose: B-D-galactopyranosyl-(1-4)-2-acetamido-2-deoxy-D-glucose(1-3)-a-D-galactopyranosyltransferase"; Carbohydrate Research, 1995, vol. 276, pp. 91-98.
Schwarz et al., "Thermodynamics of Bovine Spleen Galectin-1 Binding to Disaccharides: Correlation with Structure and Its Effect on Oligomerization at the Denaturation Temperature"; Biochemistry, 1998, vol. 37, pp. 5867-5877.

* cited by examiner

*Primary Examiner*—Shaojia Anna Jiang
*Assistant Examiner*—Jonathan S Lau
(74) *Attorney, Agent, or Firm*—Gauthier & Connors LLP

(57) ABSTRACT

The present invention relates to novel compounds, the use of said compounds as a medicament as well as for the manufacture of a medicament for treatment of disorders relating to the binding of galectin to receptors in a mammal. Said galectin is preferably a galectin-3.

14 Claims, 2 Drawing Sheets

3-TRIAZOLYL-GALACTOSIDE INHIBITORS OF GALECTINS

PRIORITY INFORMATION

This application is a continuation of International Application Serial No. PCT/SE2005/000766 filed on May 23, 2005 which claims priority to Swedish Application No. 0401301-7 filed May 21, 2004, both of which are incorporated herein by reference in their entireties.

TECHNICAL FIELD OF THE INVENTION

The present invention relates to novel compounds, the use of said compounds as medicament and for the manufacture of a medicament for the treatment of any disorder relating to the binding of a galectin receptor in mammals. The invention also relates to pharmaceutical compositions comprising of said novel compounds.

BACKGROUND ART

Galectins are proteins with a characteristic carbohydrate recognition domain (CRD) (Barondes et al., 1994; Leffler et al., 2004)(FIG. 1a). This is a tightly folded β-sandwich of about 130 aa (about 15 kDa) with the two defining features 1) a β-galactose binding site (C in FIG. 1a) and 2) sufficient similarity in a sequence motif of about seven amino acids, most of which (about six residues) make up the β-galactose binding site. However, adjacent sites (A,B,D,E in FIG. 1a) are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004; Houzelstein et al., 2004). compartments; for galectin-3, solid evidence published in well respected journals support roles in RNA splicing in the nucleus, inhibition of apoptosis in the cytosol, and a variety of extracellular effects on cell signaling and adhesion (Patterson et al., Ochieng et al., Takenaka et al., Hsu et al. and others in Leffler (editor), 2004b). Galectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals.

The present invention relates mainly to galectin-3, but its principles may be applicable also to other galectins.

Potential Therapeutic Use of Galectin-3 Inhibitors.

Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXS, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation.

A pro-inflammatory role of galectin-3 is indicated by its induction in cells at inflammatory sites, a variety of effects on immune cells (e.g. oxidative burst in neutrophils, chemotaxis in monocytes), and decrease of the inflammatory response, mainly in neutrophils and macrophages, in null mutant mice (chapters by Rabinovich et al., Sato et al., and Almkvist et al. in Leffler (editor), 2004b). Moreover, knock-out mice of Mac-2BP, a galectin-3 ligand, have increased inflammatory responses (Trahey et al., 1999). Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Septic Shock.

The idea of a possible role of galectin-3 in septic shock comes from our own studies (Almquist et al., 2001). Briefly, the argument goes as follows. It is known that septic shock involves dissemination of bacterial lipopolysaccharide into the blood stream, and that the pathological effects of this are mediated via neutrophil leukocytes (Karima et al., 1999). LPS does not activate the tissue-damaging response of the neutrophil. Instead, it primes the neutrophil, so that it is converted from unresponsive to responsive to other, presumably endogenous, activators. In septic shock, this priming happens prematurely in the blood stream. Endogenous activators could then induce the tissue damaging response in the wrong place and time. Several candidates have been proposed as these endogenous activators, including TNF-alfa. Inhibitors of these have been used in treatment schemes without much success (Karima et al., 1999). Since our own studies indicate that galectin-3 is a good candidate for being an endogenous activator of primed neutrophils (Almquist et al., 2001), galectin-3 inhibitors may be very useful in septic shock.

Treatment of Cancer.

A large number of immunohistochemical studies show changed expression of certain galectins in cancer (van den Brule et. al. and Bidon et al. in Leffler (editor), 2004b) Galectin-3 is now an established histochemical marker of thyroid cancer, and neoexpression of galectin-4 is a promising marker of early breast cancer (Huflejt and Leffler, 2004). The direct evidence for a role of galectin-3 in cancer comes from mouse models, mainly by Raz et al, but also others (Takenaka et al. in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b. Therefore, the over-expression of these galectins in cancers might help the tumor to defend itself against the T-cell response raised by the host (Rubinstein et al., 2004). Null mutant mice for galectins-1 and -3 have been established many years ago (Poirier, 2002). These are healthy and reproduce apparently normally in animal house conditions. However recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analysed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004; Ahmad et al., 2004). These were the first discovered galectins and are abundant in many tissues. However, our recent phylogenetic analysis (FIG. 2) suggest that galectins with two CRDs within a peptide chain, bi-CRD galectins, appear to be more ancient and more central to the family than previously thought and that most of mammalian mono-CRD galectins may have descended from one or the other CRD of a bi-CRD galectin.

There are now over 1200 publications on galectins in PubMed, with most, as mentioned above, about galectins-1 and -3. Strong evidence suggests roles for galectins in e.g. inflammation, cancer, and development recently reviewed in a special issue (Leffler (editor), 2004b) but a unifying model of the "basic function" of galectins at the cellular-molecular level is lacking.

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these mutant mice may make galectin inhibitors more favorable as drugs. If galectin activity contributes to pathological conditions as suggested above but less to normal conditions, then inhibition of them will have less unwanted side effects.

Known Inhibitors

Natural Ligands.

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or lacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Synthetic Inhibitors.

Saccharides coupled to amino acids with anti-cancer activity were first identified as natural compounds in serum, but subsequently, synthetic analogues have been made (Glinsky et al., 1996). Among them, those with lactose or Gal coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

A divalent form of a lactosyl-amino acid had higher potency in a solid phase assay (Naidenko et al., 2000; Huflejt et al., 2001; Huflejt and Leffler, 2004) and clusters having up to four lactose moieties showed a strong multivalency effect when binding to galectin-3, but not to galectin-1 and -5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis.

Thus, there is a need for small synthetic molecules Thiodigalactoside is known to be a synthetic and hydrolytically stable, yet polar inhibitor, approximately as efficient as N-acetyllactosamine (Leffler and Barondes, 1986). A library of pentapeptides provided inhibitors against galectin-1 and -3, but only with low affinities, similar to that of galactose (Arnusch et al., 2004). Furthermore, peptides are not ideal agents for targeting galectins in vivo, as they are susceptible to hydrolysis and are typically polar. N-Acetyllactosamine derivatives carrying aromatic amides or substituted benzyl ethers at C-3' have been demonstrated to be highly efficient inhibitors of galectin-3, with unprecedented IC$_{50}$ values as low as 4.8 μM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. However, said 3'-amido-derivatised compounds are still susceptible to hydrolytic degradation in vivo, due to the presence of a glycosidic bond in the N-acetyllactosamine disaccharide moiety and, although they are the best reported small molecule inhibitors of galectin-3, even further improved affinity is desirable.

Thus, there is still a considerable need within the art of inhibitors against galectins, in particular of galectin-3.

SUMMARY OF THE INVENTION

Therefore the present invention relates to a compound having the general formula (I):

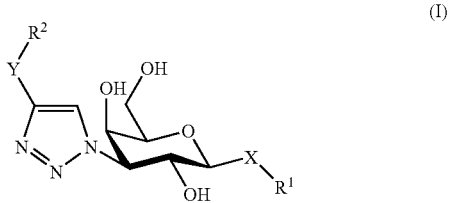

(I)

wherein
the configuration of the pyranose ring is D-galacto;
X is selected from the group consisting of O, S, NH, CH$_2$, and NR$^4$, or is a bond;
Y is selected from the group consisting of CH$_2$, CO, SO$_2$, SO, PO$_2$ and PO, phenyl, or is a bond;
R$^1$ is selected from the group consisting of;
a) a saccharide;
b) a substituted saccharide;
c) D-galactose;
d) substituted D-galactose;
e) C3-[1,2,3]-triazol-1-yl-substituted D-galactose;
f) hydrogen, an alkyl group, an alkenyl group, an aryl group, a heteroaryl group, and a heterocycle and derivatives thereof;
g) an amino group, a substituted amino group, an imino group, or a substituted imino group.
R$^2$ is selected from the group consisting of; hydrogen, an amino group, a substituted amino group, an alkyl group, a substituted alkyl group, an alkenyl group, a substituted alkenyl group, an alkynyl group, a substituted alkynyl group, an alkoxy group, a substituted alkoxy group, an alkylamino group, a substituted alkylamino group, an arylamino group, a substituted arylamino group, an aryloxy group, a substituted aryloxy group, an aryl group, a substituted aryl group, a heteroaryl group, a substituted heteroaryl group, and a heterocycle, a substituted heterocycle.

The present invention also relates to a compound according to the above-mentioned formula for use as a medicament.

Still further, the present invention relates to the use of a compound according to the above-mentioned formula for the manufacture of a medicament for the treatment of any disorder relating to the binding of a galectin to ligands in a mammal.

Yet further, the present invention relates to a pharmaceutical composition comprising a compound according to the above-mentioned formula as active ingredient together with a pharmaceutically acceptable adjuvant, diluent, excepient or carrier.

Yet further, the present invention relates to a method for inhibiting conditions associated with the binding of galectin to ligands in a mammal, which method comprises administering to said mammal an effective amount of a compound according to the above-mentioned formula.

Still further, the present invention relates to a method for inhibiting conditions associated with the binding of galectin to ligands in a mammal, which method comprises administering to said mammal an effective amount of a pharmaceutical composition mentioned above.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of Gal in lactose or LacNAc. The X-ray crystal structures of galectins-1, -2, and -3 demonstrated a highly conserved core binding site for lactose and LacNAc with features in agreement with the specificity studies (Lobsanov and Rini, 1997; Seetharaman et al., 1998). In addition, an extended groove was found, which might accommodate the added sugar residue in the longer saccharides (A-B in FIG. 1). The shape of this groove varies between galectins, suggesting that the same extensions would not be bound equally by the different galectins. Moreover, including additional galectins (e.g. galectins-4, -8 and -9) it has become clear that there is also variations in binding preference on the other side of the Gal residue (sites D-E in FIG. 1)(Leffler et al., 2004).

Structure-based Design of Substituted 3-triazolyl-galactosides as Galectin Inhibitors.

The extended binding site close to HO-3' of N-acetyllactosamine (site B, FIG. 1b) have been exploited in the design of potent galectin-3 inhibiting 3'-amido-N-acetyllactosamine derivatives. (Sörme et al., 2002) In particular, aromatic amides made efficient inhibitors by forming an energetically favorable stacking interaction with the arginine-144 guanidino group of galectin-3. The synthesis of 3'-amido-N-acetyllactosamine derivatives, by the reduction and subsequent acylation of a 3'-azido-N-acetyllactosamine derivative, is laborious and of varying efficiency. The use of azides in 1,3-dipolar cycloaddition reactions with acetylenes is one of the most efficient, reliable, and high-yielding organic reactions known and it can preferably be applied on 3-azidogalactose derivatives to give 3-[1,2,3]-triazol-1-yl galactosides as small and hydrolytically stable inhibitors potentially interacting with both subsite B and C of galectin-3 (FIG. 1). In addition, 1,3-dipolar cycloaddition reactions of acetylenes with 3'-azido-N-acetyllactosamine derivative would provide even further improved inhibitors potentially interacting with the three subsites B, C, and D (FIG. 1) as the N-acetylglucosamine residue of N-acetyllactosamine is located in subsite D. Finally, thiodigalactoside is a known inhibitor with affinity for of galectin-3 similar to that of N-acetyllactosamine. One galactose unit of thiodigalactoside binds subsite C (the galactose site) of galectins, while the other binds subsite D (the N-acetylglucosamine site). Hence, derivatization of thiodigalactose at both C3 carbons (C3 and C3') with [1,2,3]-triazol-1-yl moieties would provide bis-3,3'-[1,2,3]-triazol-1-ylthiodigalactosides potentially interacting with all four subsites B-E, which can lead to inhibitors of galectins with even better affinities. Of additional importance is that the synthesis of thiodigalactosides is straight-forward and economical in comparison to the synthesis of N-acetyllactosamine derivatives, and that the thio-glycosidic linkage of thiodigalactosides is more hydrolytically stable than O-glycosidic linkages resulting in longer half-life in vivo.

DETAILED DESCRIPTION OF THE PREFERRED EMBODIMENTS OF THE INVENTION

Figure 1A:
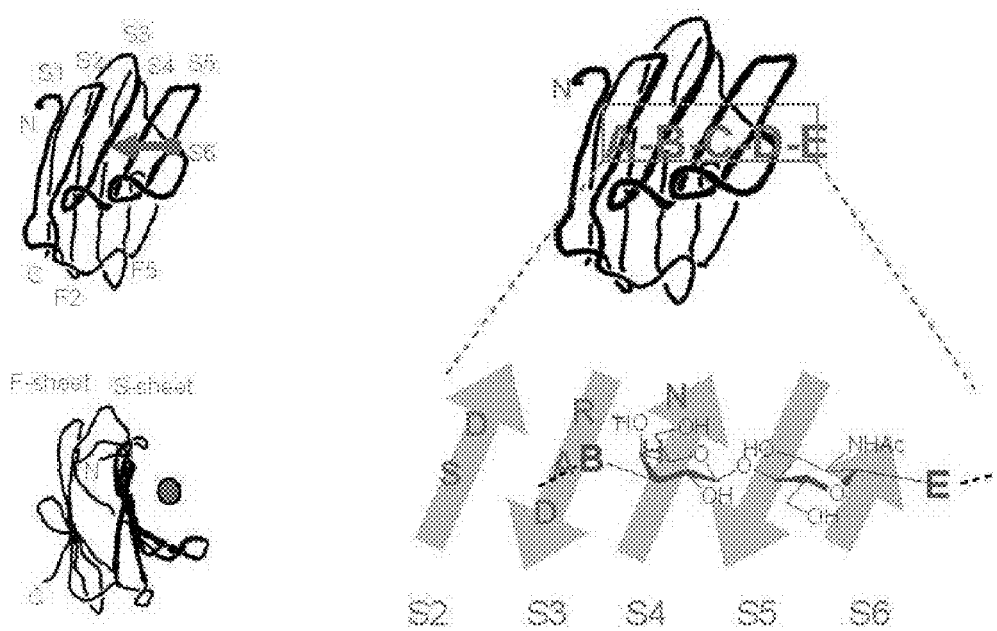
FIG. 1. a) Schematic of the galectin carbohydrate recognition domain (CRD)(left) and carbohydrate binding sites (right)(Barondes et al., 1994; Leffler et al., 2004). The CRD is shown in face and side view with bound disaccharide symbolized by arrow or dot (left). It consists of two β-sheets named S and F. The concave side of the S-sheets forms a groove that can hold about a tetrasaccharide and has four subsites (A-D) with the defining galactose binding site as C, and a fifth subsite (E) outside the groove (top right). A bound LacNAc is shown on the S-beta sheet (bottom right) with extensions into subsite B and E. Pertinent amino acids in galectin-3 around subsite B are indicated in one letter code (grey). b) Structure of carbohydrate recognition site of galectin-3 CRD (smooth surface) with bound LacNAc (stick model). The subsites described in FIG. 1a are indicated below figure with Gal in site C. The arrows indicate spaces in site B targeted by derivatization on position 3 of the Gal (Sörme et al., 2002). Selected amino acids are named. The GlcNAc of the LacNAc is in site D.
Figure 1B:
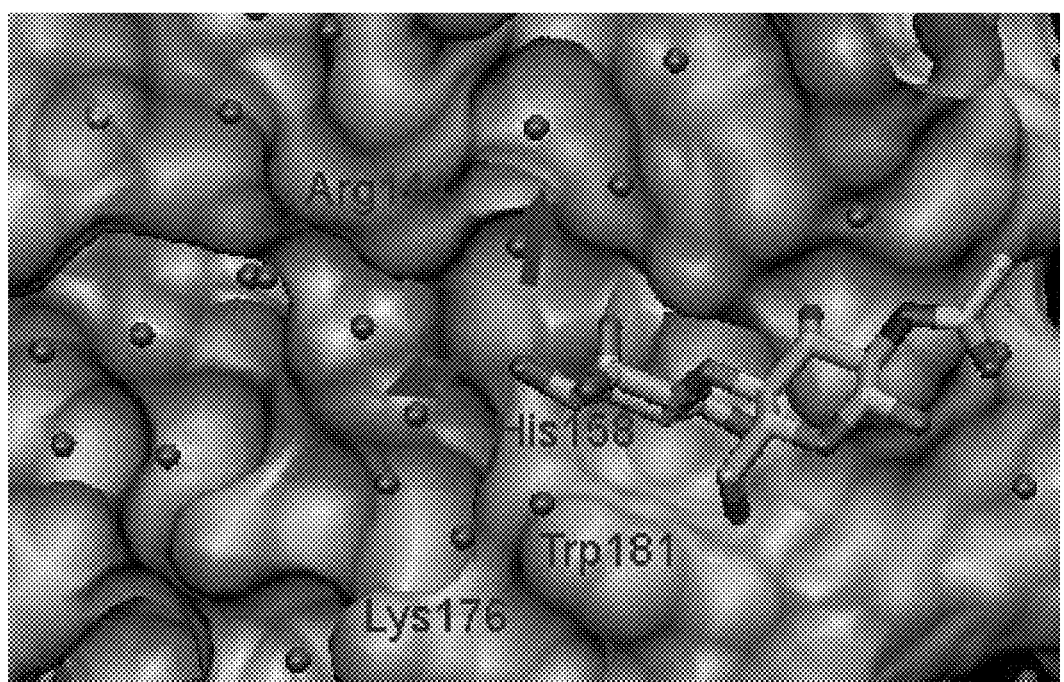
Figure 2:
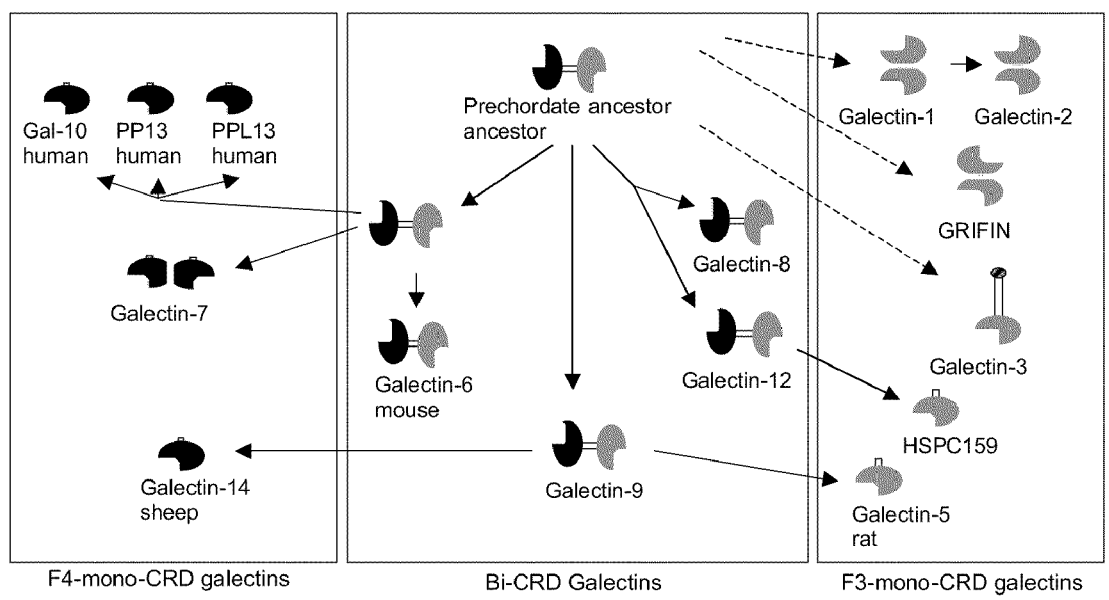
FIG. 2. Mammalian galectins and their phylogeny from a prechordate ancestor (Houzelstein et al., 2004). All the CRDs are of either of two types (F4 and F3, black and grey respectively) defined by corresponding gene structure (intron-exon boundaries) and supported by their respective sequence relationships. The ancestral prechordate galectins include a bi-CRD galectin with one of each CRD type (most likely derived in much earlier evolution from duplication of a mono-CRD galectin). Large scale duplication of genome fragments in early chordate-vertebrate evolution give rise to the four major bi-CRD galectins found in mammals. Local duplication-deletion events give rise to mono-CRD galectins related to either the N- or C-terminal CRD. Some of these occurred at early more uncertain times (dotted arrows) whereas other are recent and more certain (filled arrows). Recent duplications have also produced extra copies of bi-CRD galectins in certain mammals (e.g. two extra copies of galectin-9s in humans (not shown); galectin-6 in mouse).

According to one aspect of the invention, in the above-mentioned formula, X is S or O and Y is a phenyl or a carbonyl group.

In the present disclosure, the term "alkyl group" is meant to comprise from 1 to 12 carbon atoms. Said alkyl group may be straight- or branched-chain. Said alkyl group may also form a cycle comprising from 3 to 12 carbon atoms.

In the present disclosure, the term "alkenyl group" is meant to comprise from 2 to 12 carbon atoms. Said alkenyl group comprises at least one double bond.

In the present disclosure the term "aryl group" is meant to comprise from 4 to 18 carbon atoms. Said aryl group may be a phenyl group or a naphthyl group.

In the present disclosure, the term "alkoxy group" is meant to comprise from 1 to 12 carbon atoms. Said alkoxy group may be a methoxy group or an ethoxy group.

In the present disclosure, the term "alkylamino group" is meant to comprise from 1 to 12 carbon atoms.

In the present disclosure, the term "arylamino group" is meant to comprise from 4 to 12 carbon atoms. Said "arylamino group" may be aniline, carboxylated aniline or halogenated aniline.

In the present disclosure, the term "aryloxy group" is meant to comprise from 4 to 12 carbon atoms. Said "aryloxy group" may be phenol, carboxylated phenol or halogenated phenol.

In the present disclosure, the term "heteroaryl group" is meant to comprise from 4 to 18 carbon atoms, wherein at least one atom of the ring is a heteroatom, i.e. not a carbon. Preferably, said heteroatom is N, O or S. Said heteroaryl group may be a quinoline, isoquinoline, pyridine, a pyrrole, a furan or a thiophene group.

The above-mentioned groups may naturally be substituted with any other known substituents within the art of organic chemistry.

The groups may also be substituted with two or more of the substituents. Examples of substituents are halogen, alkoxy, nitro, sulfo, amino, hydroxy, and carbonyl groups.

In yet another aspect of the invention, said compound is methyl 3-deoxy-3-(1H-[1,2,3]-triazol-1-yl)-1-thio-β-D-galactopyranoside (8), methyl 3-deoxy-3-(4-propyl-1H-[1,2,3]-triazol-1-yl)-1-thio-β-D-galactopyranoside (9), methyl 3-(4-methoxycarbonyl-1H-[1,2,3]-triazol-1-yl)-3-deoxy-1-thio-β-D-galactopyranoside (10), methyl 3-deoxy-3-(4-(1-hydroxy-1-cyclohexyl)-1H-[1,2,3]-triazol-1-yl)-1-thio-β-D-galactopyranoside (11), methyl 3-deoxy-3-(4-phenyl-1H-[1,2,3]-triazol-1-yl)-1-thio-β-D-galactopyranoside (12), methyl 3-deoxy-3-(4-p-tolylsulfonyl-1H-[1,2,3]-triazol-1-yl)-1-thio-β-D-galactopyranoside (13), methyl 3-(4-methylaminocarbonyl-1H-[1,2,3]-triazol-1-yl)-3-deoxy-1-thio-β-D-galactopyranoside (14), methyl 3-(4-butylaminocarbonyl-1H-[1,2,3]-triazol-1-yl)-3-deoxy-1-thio-β-D-galactopyranoside (15), methyl 3-(4-benzylaminocarbonyl-1H-[1,2,3]-triazol-1-yl)-3-deoxy-1-thio-β-D-galactopyranoside (16), methyl 3-{4-(3-hydroxyprop-1-ylaminocarbonyl)-1H-[1,2,3]-triazol-1-yl}-3-deoxy-1-thio-β-D-galactopyranoside (17), methyl 3-{4-[2-(N-morpholino)-ethylaminocarbonyl]-1H-[1,2,3]-triazol-1-yl}-3-deoxy-1-thio-β-D-galactopyranoside (18), methyl 3-(4-methylaminocarbonyl-1H-[1,2,3]-triazol-1-yl)-3-deoxy-β-D-galactopyranosyl-(11-4)-2-acetamido-2-deoxy-β-D-glucopyranoside (21), bis-(3-deoxy-3-(4-(methylaminocarbonyl)-1H-[1,2,3]-triazol-1-yl)-β-D-galactopyranosyl)sulfane (26), methyl 3-deoxy-3-{4-(2-fluorophenyl)-1H-[1,2,3]-triazol-1-yl}-1-thio-β-D-galactopyranoside, methyl 3-deoxy-3-{4-(2-methoxyphenyl)-1H-[1,2,3]-triazol-1-yl}-1-thio-β-D-galactopyranoside, methyl 3-deoxy-3-{4-(3-methoxyphenyl)-1H-[1,2,3]-triazol-1-yl}-1-thio-β-D-galactopyranoside, methyl 3-deoxy-3-{4-(4-methoxyphenyl)-1H-[1,2,3]-triazol-1-yl}-1-thio-β-D-galactopyranoside, methyl 3-deoxy-3-{4-(3,5-dimethoxyphenyl)-1H-[1,2,3]-triazol-1-yl}-1-thio-β-D-galactopyranoside, methyl 3-deoxy-3-{4-(1-naphthyl)-1H-[1,2,3]-triazol-1-yl}-1-thio-β-D-galactopyranoside, methyl 3-deoxy-3-{4-(2-naphthyl)-1H-[1,2,3]-triazol-1-yl}-1-thio-β-D-galactopyranoside, methyl 3-deoxy-3-{4-(2-pyridyl)-1H-[1,2,3]-triazol-1-yl}-1-thio-β-D-galactopyranoside,
methyl 3-deoxy-3-{4-(3-pyridyl)-1H-[1,2,3]-triazol-1-yl}-1-thio-β-D-galactopyranoside,
methyl 3-deoxy-3-{4-(4-pyridyl)-1H-[1,2,3]-triazol-1-yl}-1-thio-β-D-galactopyranoside,
O-{3-deoxy-3-[4-phenyl-[1H-[1,2,3]-triazol-1-yl]-β-D-galactopyranosyl}-3-indol-carbaldoxim,
O-{3-deoxy-3-[4-(methylaminocarbonyl)-1H-[1,2,3]-triazol-1-yl]-β-D-galactopyranosyl}-3-indol-carbaldoxim,
O-{3-deoxy-3-[4-phenyl-[1H-[1,2,3]-triazol-1-yl]-β-D-galactopyranosyl}-(2-hydroxy-5-nitro-phenyl)-carbaldoxim,
O-{3-deoxy-3-[4-(methylaminocarbonyl)-1H-[1,2,3]-triazol-1-yl]-β-D-galactopyranosyl}-(2-hydroxy-5-nitro-phenyl)-carbaldoxim,
O-{3-deoxy-3-[4-phenyl-[1H-[1,2,3]-triazol-1-yl]-β-D-galactopyranosyl}-(2,5-dihydroxyphenyl)-carbaldoxim,
O-{3-deoxy-3-[4-(methylaminocarbonyl)-1H-[1,2,3]-triazol-1-yl]-β-D-galactopyranosyl}-(2,5-dihydroxyphenyl)-carbaldoxim,
O-{3-deoxy-3-[4-phenyl-[1H-[1,2,3]-triazol-1-yl]-β-D-galactopyranosyl}-1-naphthyl-carbaldoxim,
O-{3-deoxy-3-[4-(methylaminocarbonyl)-1H-[1,2,3]-triazol-1-yl]-β-D-galactopyranosyl}-1-naphthyl-carbaldoxim.

In one aspect, the present invention relates to the use of a compound according to the above-mentioned formula for the manufacture of a medicament for the treatment of any disorder relating to the binding of a galectin to receptors in a mammal. In one aspect of the invention, said galectin is galectin-3.

In another aspect, the invention relates to the use of a compound according to the above-mentioned formula for the manufacture of a medicament for the treatment of a disorder being selected from the group consisting of inflammation, septic shock, cancer, and autoimmune diseases such as reumatoid artrit and multiple schlerosis. Preferably, said compound is for the manufacture of a medicament for the treatment of cancer.

In yet another aspect, the present invention relates to a pharmaceutical composition comprising a compound according to the above-mentioned formula as active ingredient together with a pharmaceutically acceptable adjuvant, diluent, excepient or carrier. A pharmaceutical composition of the invention comprises from 1 to 99 weight % of a pharmaceutically acceptable adjuvant, diluent, excepient or carrier and from 1 to 99 weight % of a compound according to above mentioned formula.

In one aspect, the invention relates to a method for inhibiting conditions associated with the binding of galectin to receptors in a mammal which method comprises administering to said mammal, an effective amount of a compound according to the above-mentioned formula. In one particularly important aspect of the invention, said galectin is galectin-3.

In another aspect, the invention relates to a method for inhibiting conditions associated with the binding of galectin to receptors in a mammal, which method comprises administering to said mammal an effective amount of a pharmaceutical composition according to the above. In one particularly important aspect of the invention, said galectin is galectin-3.

The pharmaceutical composition according to the present invention comprising a compound of the invention may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition of the present invention may be in the form of, for example, tablets, capsules, powders, solutions, transdermal patches or suppositories.

The pharmaceutical composition of the present invention may optionally comprise two or more compounds of the present invention. The composition may also be used together with other medicaments within the art for the treatment of related disorders.

The typical dosages of the compounds of the present invention vary within a wide range and depend on many factors, such as the route of administration, the requirement of the individual in need of treatment, the individual's body weight, age and general condition.

The adjuvants, diluents, excepients and/or carriers that may be used in the composition of the invention must be pharmaceutically acceptable in the sense of being compatible with the compounds and the other ingredients of the pharmaceutical composition, and not deleterious to the recipient thereof. The adjuvants, diluents, excepients and carriers that may be used in the pharmaceutical composition of the invention are well known to a person within the art.

Synthesis of Triazoles

The 3-azido-galactoside derivative 1 was converted to the triazoles 2 and 7 by heating with the corresponding alkyne in toluene. Triazoles 3-6 were synthesized under Cu⁺ catalysis (Tornøe et al., 2002), where the azide 1 was reacted with the appropriate alkynes in the presence of copper iodide (Scheme 1). Compounds 2-7 were deprotected by treatment with methanolic sodium methoxide or with methylamine in water to give the triazole inhibitors 8-13.

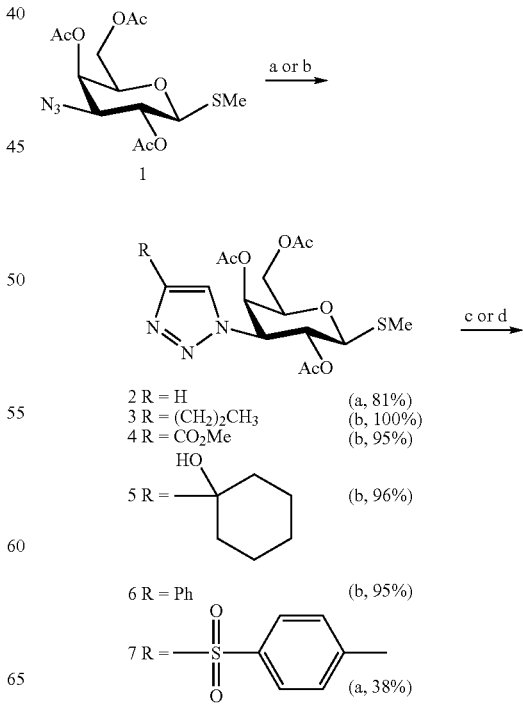

Scheme 3:

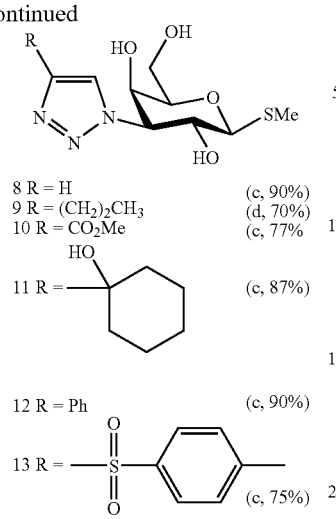

8 R = H (c, 90%)
9 R = (CH₂)₂CH₃ (d, 70%)
10 R = CO₂Me (c, 77%)
11 R = [1-hydroxycyclohexyl] (c, 87%)
12 R = Ph (c, 90%)
13 R = —SO₂—C₆H₄—CH₃ (c, 75%)

a) Toluene, 100° C.
b) Alkyne, CuI, iPrEt₂N, toluene.
c) MeNH₂, H₂O.
d) NaOMe, MeOH.

The methyl ester 3 could simultaneously be de-O-acetylated and transformed into primary amides 14-18 by treatment with the corresponding primary amine in water or methanol (Scheme 2).

Scheme 2.

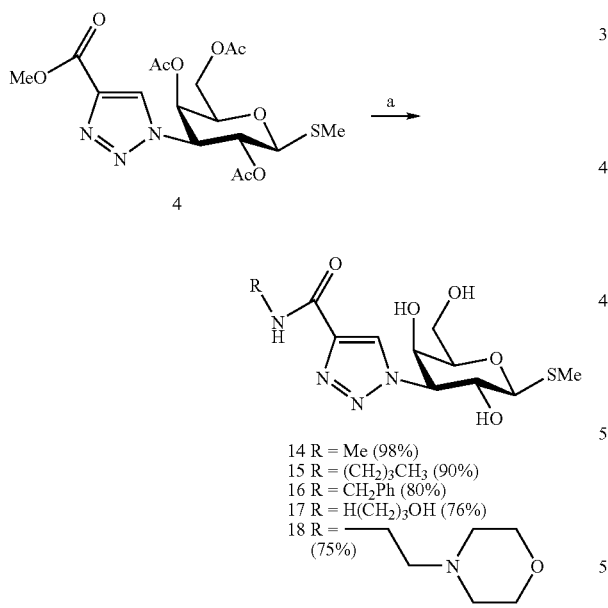

14 R = Me (98%)
15 R = (CH₂)₃CH₃ (90%)
16 R = CH₂Ph (80%)
17 R = H(CH₂)₃OH (76%)
18 R = [CH₂CH₂-morpholinyl] (75%)

a) Amine, water or MeOH.

A 3'-deoxy-3'-triazol-1-yl derivative of N-acetyllactosamine 21 was synthesized by reacting the corresponding 3'-azido derivative 19 with methyl propiolate under copper iodide catalysis to give the methyl ester 20, followed by simultaneous de-O-acetylation and methyl amide formation by treatment with methylamine in water.

Scheme 3.

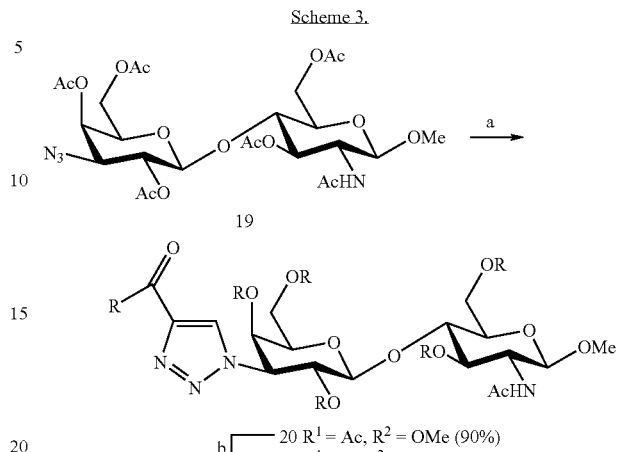

20 R¹ = Ac, R² = OMe (90%)
21 R¹ = H, R² = NHMe (80%)

a) Methyl propiolate, CuI, iPrEt₂N, toluene.
b) Methylamine, water.

A 3,3'-bis-triazol-1-yl derivative of thiodigalactoside 26 was synthesized from the acetylated 3-azido-3-deoxy galactose 22 (Lowary and Hindsgaul, 1994). Compound 22 was subjected to methyl propiolate in the presence of copper iodide to give the triazole derivative 23. Bromination of 23 gave the labile α-D-galactopyranosyl bromide 24, which was immediately dimerized to the protected 3,3'-bis-triazol-1-yl thiodigalactoside derivative 25. Simultaneous de-O-acetylation and methyl amide formation of 25 by treatment with methylamine in water gave 26.

Scheme 4.

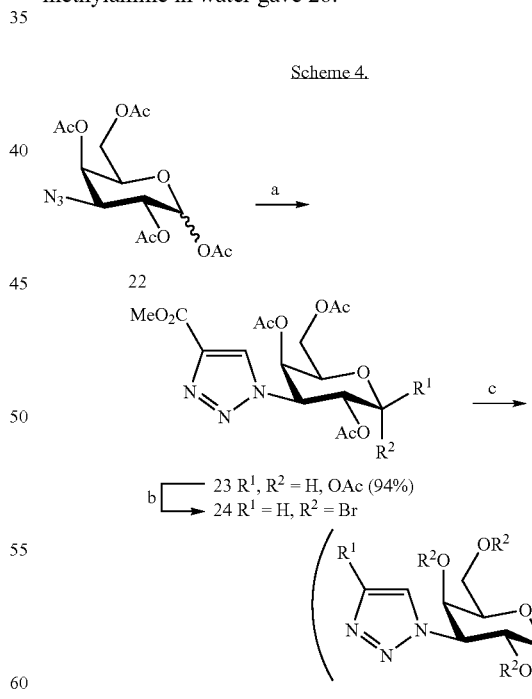

23 R¹, R² = H, OAc (94%)
24 R¹ = H, R² = Br

25 R¹ = CO₂Me, R² = OAc (58%)
26 R¹ = CONHMe, R² = H (62%)

a) Methyl propiolate, CuI, iPrEt₂N, toluene.
b) CH₂Cl₂, Ac₂O, 33% HBr/AcOH.
c) Na₂S, MS 4Å, MeCN.
d) Methylamine, water.

Evaluation of $K_d$ Values Against Galectin-3

Compounds 8-18, 21, and 26 were evaluated for their efficiency in inhibiting galectin-3 in a known fluorescence polarization-based assay (Sörme et al., 2003a, 2004). (Table 1). The known inhibitors 27, 28, and 29 of galectin-3 were included as reference compounds. All novel galactosides carrying a 4-substituted triazol-1-yl group at C3 (9-18, $K_d$ 141-4615 µM) were significantly better inhibitors of galectin-3 than the reference galactoside 27 ($K_d$ 5337 µM). In particular, the phenyl (12), tosyl (13), butylamide (15), and benzyl amide (16) derivatives were unexpectedly powerful inhibitors with $K_d$ of 107-147 µM, which is 50-fold improvement in comparison with the reference inhibitor 27 and unprecedented within the field of monosaccharide-derived inhibitors of galectins.

N-Acetyllactosamine is a better natural ligand to galectin-3 than galactose is. Hence, the 3'-triazol-1-yl N-acetyllactosamine compound 21 ($K_d$ 5.8 µM) was clearly better than the corresponding galactose compound 14 and than the standard reference inhibitor N-acetyllactosamine derivative 28. Compound 21 is as good inhibitor of galectin-3 as the reported best inhibitors (Sörme et al., 2002).

Thiodigalactoside 29 is a well-known inhibitor with affinity for galectin-3 similar to that of N-acetyllactosamine. Hence, the 3,3'-bis-triazol-1-yl thiodigalactoside 26 ($K_d$ 150 nM) was also much better than the corresponding galactose compound 14 and than the standard reference inhibitors N-acetyllactosamine derivative 28 and thiodigalactoside 29.

The unexpectedly high inhibitor potency of 21 and 26 against galectin-3 renders them suitable to be active components in pharmaceutical compositions targeting conditions where galectin-3 plays a pathogenic role. The ease of preparation of compounds 21 and 26, via the high-yielding 1,3-dipolar cycloaddtion between the azides and acetylene derivatives, add further value to them as inhibitors of galectins. In particular, the bis-3,3'-[1,2,3]-triazol-1-yl-thiodigalactoside 26 is a valuable inhibitor in view of its unprecedented high affinity, efficient and economical synthesis, and expected longer in vivo half-life. The unnatural aromatic [1,2,3]-triazol-1-yl substituents, as well as the thio-glycosidic linkage of 26, can be expected to improve hydrolytic stability and improve absorption in the gastrointestinal tract.

TABLE 1

Affinity of compounds for galectin-3 as calculated from test by fluorescence polarization.

| | Structure | Tested Conc. (µM) | Calculated $K_d$ (µM) |
|---|---|---|---|
| 8 | 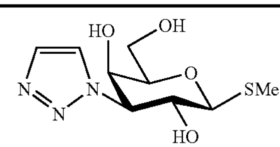 | 5000 | 21000 |
| 9 | 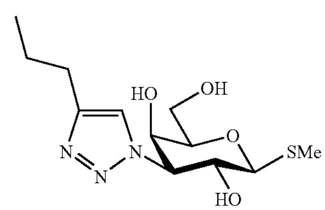 | 5000 | 4615 |
| 10 | 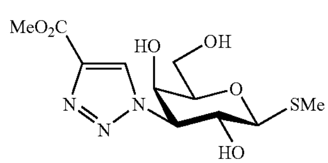 | 100 | 1408 |
| 11 | 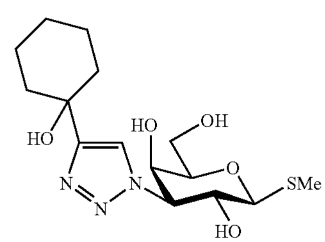 | 1000 | 1377 |
| 12 | 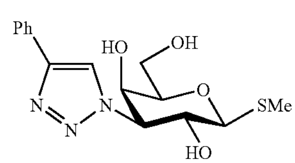 | 200 | 147 |

TABLE 1-continued

Affinity of compounds for galectin-3 as calculated from test by fluorescence polarization.

| | Structure | Tested Conc. (μM) | Calculated $K_d$ (μM) |
|---|---|---|---|
| 13 | | 200 | 141 |
| 14 | | 1000 | 230 |
| 15 | | 200 | 124 |
| 16 | | 200 | 107 |
| 17 | | 1000 | 386 |
| 18 | | 1000 | 571 |
| 21 | | 8 | 5.8 |

TABLE 1-continued

Affinity of compounds for galectin-3 as calculated from test by fluorescence polarization.

| Structure | Tested Conc. (µM) | Calculated $K_d$ (µM) |
|---|---|---|
| 26 [structure] | 1.6 | 0.15 |
| Reference inhibitors: | | |
| 27 [structure] | 5000 | 5337 |
| 28 [structure] | 40 | 52 |
| 29 [structure] | 40 | 43 |

Methodology/Experimental

General Synthetic Procedures

The compounds of this invention may be prepared by the following general methods and procedures. The galectin-3 assays of this invention may be performed by the following general methods and procedures. It should be appreciated that where typical or preferred process conditions (e.g. reaction temperatures, times, molar ratios of reactants, solvents, pressures, pH etc) are given, other process conditions may also be used unless otherwise stated. Optimum reaction conditions may vary with the particular reactants, solvents used and pH etc., but such conditions can be determined by one skilled in the art by routine optimization procedures.

NMR-spectra were recorded with a Bruker DRX-400 instrument. Chemical shifts are given in ppm, with reference to internal residual solvent peaks. Chemical shifts and coupling constants were obtained from $^1$H-NMR and proton resonances were assigned from COSY experiments. High-resolution FAB mass spectra (HRMS) were recorded with a JEOL SX-120 instrument. Fluorescence polarization experiments were performed on a PolarStar instrument (BMG, Offenburg; Germany). Column chromatography was performed on SiO$_2$ (Matrex, 60 Å, 35-70 µm, Grace Amicon) and TLC was carried out on SiO$_2$ 60 F$_{254}$ (Merck) with detection under UV light and developed with aqueous sulfuric acid. Concentrations were made using rotary evaporation with bath temperature at or below 40° C. CH$_2$Cl$_2$ and CH$_3$CN were dried by distillation from CaH$_2$. Microwell plates were from Costar, Corning, N.Y. (black polystyrene). Recombinant human galectin-3 was produced in *Escherichia coli* and purified as previously described (S. M. Massa et al, 1993). PBS was 118 mM NaCl, 67 mM Na/K-phosphate, pH 7.2, 2 mM EDTA, 4 mM β-mercaptoethanol.

Synthesis of 3-triazolyl-galactosides

Typical Procedures for the Synthesis of a 3-triazolyl-galactoside Derivative:

General Procedures for the Preparation of 3-triazolyl-galactosides.

Method A: A mixture of methyl 2,4,6-tri-O-acetyl-3-azido-3-deoxy-1-thio-β-D-galactopyranoside (Sörme et al., 2002) (10 mg, 0.028 mmol) and the corresponding acetylene (4 eq.) in toluene (1.5 mL) were heated at 100° C. for 12 h. After evaporation of the solvent, the product was purified by column chromatography using the eluent indicated.

Method B: A mixture of methyl 2,4,6-tri-O-acetyl-3-azido-3-deoxy-1-thio-β-D-galactopyranoside (Sörme et al., 2002) (10 mg, 0.028 mmol), the acetylene derivative (1 eq.), copper iodide (0.5 mg, 0.1 eq.), diisopropylethylamine (1 eq.) and toluene (1 mL) were stirred for (t) time at (T) temperature. The solvent was evaporated and the product was purified by column chromatography using the eluent indicated.

Methyl 2,4,6-tri-O-acetyl-3-(1H-[1,2,3]-triazol-1-yl)-3-deoxy-1-thio-β-D-galactopyranoside (2)

Method A, x=propiolic acid, Column $SiO_2$, heptane:EtOAc 3:2, yield 8.7 mg, 81%.
$^1$H NMR (400 MHz, $CDCl_3$) δ 7.67(bd, 1H, $J_{H,H}$=0.8, triazole), 7.61(bd, 1H, triazole), 5.71(dd, 1H, $J_{2,3}$=11-0, H-2), 5.57(d, 1H, H-4), 5.19(dd, 1H, $J_{3,4}$=3.2, H-3), 4.56(d, 1H, $J_{1,2}$=9.5, H-1), 4.14(s, 3H, H-5, 2H-6), 2.25, 2.05, 2.04, 1.91 (each s, each 3H, $4CH_3$).
$^{13}$C NMR (100.6 MHz, $CDCl_3$) δ 170.3, 169.5, 168.6 (3C=O), 133.8, 122.0(C-4', C-5'), 84.1(C-1), 75.3(C-5), 68.7(C-4), 65.4(C-2), 62.7(C-3), 61.3(C-6), 20.6, 20.4, 20.3 ($3CH_3C$=O), 11.5($CH_3S$).
MALDI-TOF MS for $C_{15}H_{22}N_3O_7S$ $[M+H]^+$ 388.

Methyl 2,4,6-tri-O-acetyl-3-deoxy-3-(4-propyl-1H-[1,2,3]-triazol-1-yl)-1-thio-β-D-galactopyranoside (3)

Method B, x=1-pentyne, t=3 days, T=50° C., Column $SiO_2$, heptane:EtOAc 5:2, yield 11.9 mg, 100%.
$^1$H NMR (400 MHz, $CDCl_3$) δ 7.31 (s, 1H, H-5'), 5.66 (dd, 1H, $J_{2,3}$=11.1, H-2), 5.55(d, 1H, H-4), 5.12(dd, 1H, $J_{3,4}$=3.2, H-3), 4.53(d, 1H, $J_{1,2}$=9.5, H-1), 2.65(td, 2H, $J_{H,H}$=7.2 , $J_{H,H}$=1.4 , $CH_2Ar$), 2.24, 2.05, 2.04, 1.91(each s, each 3H, $4CH_3$), 1.69-1.57(m, 2H, $CH_2$), 0.89(t, 3H, $J_{H,H}$=7.3 , $CH_3CH_2$).
$^{13}$C NMR (100.6 MHz, $CDCl_3$) δ 170.3, 169.5, 168.5 (3C=O), 148.3(C-4'), 119.1(C-5'), 84.2(C-19, 75.3(C-5), 68.8(C-4), 65.5(C-2), 62.6(C-3), 61.3(C-6), 27.4($CH_2Ar$), 22.6($CH_2$), 20.5, 20.4, 20.3($3CH_3C$=O), 13.3($CH_2$), 11.5 ($CH_3S$).
MALDI-TOF MS for $C_{18}H_{28}N_3O_7S$ $[M+H]^+$ 430.

Methyl 2,4,6-tri-O-acetyl-3-deoxy-3-(4-methoxycarbonyl-1H-[1,2,3]-triazol-1-yl)-1-thio-β-D-galactopyranoside (4)

Method B, x=methyl propiolate, t=12 h, T=r.t., Column $SiO_2$, heptane:EtOAc 3:2; yield 11.6 mg, 95%.
$^1$H NMR (400 MHz, $CDCl_3$) δ 8.14 (s, 1H, H-5'), 5.70 (dd, 1H, $J_{1,2}$=9.5, H-1), 5.57 (d, 1H, $J_{3,4}$=3.2, H-4), 5.18 (dd, 1H, H-3), 4.55 (d, 1H, $J_{1,2}$=9.5, H-1), 4.14 (m, 3H, H-5, 2×H-6), 3.93 (s, 3H, $CH_3O$), 2.25, 2.08, 2.04, 1.92(4s, each 3H, $CH_3$).
$^{13}$C NMR (100.6 MHz, $CDCl_3$) δ 170.7, 169.9, 169.2, 161.0 (4C=O), 140.6 (C-4'), 126.8 (C-5'), 84.6 (C-1), 75.8 (C-5), 68.9 (C-4), 65.9 (C-2), 63.8 (C-3), 61.7 (C-6), 52.7 ($CH_3O$), 21.0, 20.9, 20.8 (3 $CH_3C$=O), 11.9 ($CH_3S$).
MALDI-TOF MS for $C_{17}H_{24}N_3O_9S$ $[M+H]^+$ 446.

Methyl 2,4,6-tri-O-acetyl-3-deoxy-3-(4-(1-hydroxy-1-cyclohexyl)-1H-[1,2,3]-triazol-1-yl)-1-thio-β-D-galactopyranoside (5)

Method B, x=1-ethynyl-1-cyclohexanol, t=12 h, T=r.t., Column $SiO_2$, heptane:EtOAc 3:2, yield 12.0 mg, 96%.
$^1$H NMR (400 MHz, $CDCl_3$) δ 7.49(s, 1H, H-5'), 5.67(dd, 1H, $J_{2,3}$=11-0, H-2), 5.54 (d, 1H, H-4), 5.13(dd, 1H, $J_{3,4}$=3.2, H-3), 4.55 (d, 1H, $J_{1,2}$=9.6, H-1), 4.13 (s, 3H, H-5, 2H-6), 2.24, 2.05, 2.04, 1.91(each s, each 3H, $4CH_3$), 1.81-1.25(m, 11H, cyclohexyl).
$^{13}$C NMR (100.6 MHz, $CDCl_3$) δ 170.3, 169.4, 168.6 (3C=O), 155.7(C-4'), 118.4(C-5'), 84.1(C-1), 75.3(C-5), 69.4(C-1cyclohexyl), 68.8(C-4), 65.5(C-2), 62.7(C-3), 61.3 (C-6), 38.1, 38.0, 25.2, 21.9, 21.8(Cyclohexyl), 20.5, 20.4, 20.3($3CH_3C$=O), 11.5($CH_3S$).
MALDI-TOF MS for $C_{21}H_{32}N_3O_8S$ $[M+H]^+$ 486.

Methyl 2,4,6-tri-O-acetyl-3-deoxy-3-(4-phenyl-1H-[1,2,3]-triazol-1-yl)-1-thio-β-D-galactopyranoside (6)

Method B, x=phenyl acetylene, t=3 days, T=r.t., Column $SiO_2$, heptane:EtOAc 5:2; yield 12.1 mg (95%).
$^1$H NMR (400 MHz, $CDCl_3$) δ 7.82 (s, 1H, H-5'), 7.80-7.78 (m, 2H, o-Ph), 7.44-7.40 (m, 2H, p-Ph), 7.34 (tt, 1H, $J_{o,m}$=7.3, $J_{o,p}$=1, p-Ph), 5.76 (dd, 1H, $J_{2,3}$=11.0, H-2), 5.62 (d, 1H, H-4), 5.19 (dd, 1H, $J_{3,4}$=3.2, H-3), 4.57 (d, 1H, $J_{1,2}$=9.5, H-1), 4.15 (s, 3H, H-4), 2.27 (s, 3H, $CH_3S$), 2.06, 2.05, 1.93 (3s, each 3H, $CH_3C$=O).
$^{13}$C NMR (100.6 MHz, $CDCl_3$) δ 170.3, 169.6, 168.6 (3C=O), 147.8 (C-4'), 129.9, 128.8, 128.3, 128.6, 117.9 (C-5'), 84.1 (C-1), 75.4 (C-5), 68.8 (C-4), 65.4 (C-2), 62.9 (C-3), 61.4 (C-6), 20.6, 20.4, 20.3 (3 $CH_3C$=O), 11.5 ($CH_3S$).
MALDI-TOF MS for $C_{21}H_{26}N_3O_7S$ $[M+H]^+$ 464.

Methyl 2,4,6-tri-O-acetyl-3-(4-p-tolylsulfonyl-1H-[1,2,3]-triazol-1-yl)-3-deoxy-1-thio-β-D-galactopyranoside (7)

Method A, x=1-ethynyl-p-tolyl sulfone, Column $SiO_2$, heptane:EtOAc 5:1 gradient 7:2, yield 5.7 mg, 38%.
$^1$H NMR (400 MHz, $CDCl_3$) δ 8.17(s, 1H, H-5'), 7.88(d, 2H, $J_{H,H}$=8.4, Ph), 7.33(d, 2H, Ph), 5.64(dd, 1H, $J_{2,3}$=11.0, H-2), 5.51(d, 1H, H-4), 5.15(dd, 1H, $J_{3,4}$=3.2, H-3), 4.53(d, 1H, $J_{1,2}$=9.5, H-1), 4.12(m, 3H, H-5, 2H-6), 2.42(s, 3H, $CH_3Ph$), 2.23(s, 3H, $CH_3S$), 2.03, 2.00, 1.87(each s, each 3 h, $3CH_3C$=O).
$^{13}$C NMR (100.6 MHz, $CDCl_3$) δ 170.2, 169.3, 168.6 (3C=O), 149.5, 145.0, 139.9(C-4', C-1PH, C-4PH), 129.8, 127.9(each 2C, PH), 124.9(C-5'), 83.9(C-1), 75.2(C-5), 68.3 (C-4), 65.2(C-2), 63.5(C-3), 61.1(C-6), 21.6, 20.5, 20.3, 20.1 ($3CH_3C$=O, $CH_3PH$), 11.4($CH_3S$).
FAB HRMS Calcd. for $C_{22}H_{27}O_9N_3S_2Na$ $[M+Na]^+$ 564.1086; found 564.1093.

General Procedure for Deprotection of Compounds 2-3 and 5-7 to Give 8-9 and 11-13:

The protected sugar (10 mg) was dissolved in methylamine (40% solution in water, 2 mL) and stirred overnight. After this time, the mixture was evaporated and the product was purified by column chromatography.

Methyl 3-deoxy-3-(1H-[1,2,3]-triazol-1-yl)-1-thio-β-D-galactopyranoside (8)

Column $SiO_2$, $CH_2Cl_2$:MeOH 17:1, yield 6.0 mg, 90%.
$^1$H NMR (400 MHz, MeOD) δ 8.08(d, 1H, $J_{H,H}$=1.0, triazole), 7.74(d, 1H, triazole), 4.83(dd, 1H, $J_{3,4}$=3.0, $J_{2,3}$=10.5, H-3), 4.46(d, 1H, $J_{1,2}$=9.4, H-1), 4.20(dd, 1H, H-2), 4.09(d, 1H, H-4), 3.80-3.66(m, 3H, H-5, 2H-6), 2.25(s, 3H, $CH_3S$).
$^{13}$C NMR (100.6 MHz, MeOD) δ 133.8, 125.4(C-4', C-5'), 88.7(C-1), 81.0(C-5), 69.8(C-4), 68.8(C-3), 67.7(C-2), 62.4 (C-6), 12.6($CH_3S$).
FAB HRMS Calcd. for $C_9H_{15}N_3O_4SNa$ $[M+Na]^+$ 284.0681; found 284.0677.

Methyl 3-deoxy-3-(4-propyl-1H-[1,2,3]-triazol-1-yl)-1-thio-β-D-galactopyranoside (9)

Column SiO$_2$, CH$_2$Cl$_2$:MeOH 20:1, yield 5.5 mg, 77%.

$^1$H NMR (400 MHz, MeOD) δ 7.82(s, 1H, H-5'), 4.72(dd, 1H, J$_{3,4}$=3.0, H-3), 4.44(d, 1H, J$_{1,2}$=9.4, H-1), 4.17(dd, 1H, J$_{2,3}$=10.4, H-2), 4.07(d, 1H, H-4), 3.78-3.67(m, 3H, H-5, 2H-6), 2.67(t, 2H, J$_{H,H}$=7.5, CH$_2$), 2.25(s, 3H, CH$_3$S), 1.69 (m, 2H, CH$_2$), 0.97(t, 3H, J$_{H,H}$=7.3, CH$_3$).

$^{13}$C NMR (100.6 MHz, MeOD) δ 148.4(C-4'), 122.8(C-5'), 88.8(C-1), 81.1(C-5), 69.8(C-4), 68.8(C-3), 67.7(C-2), 62.4 (C-6), 28.5(CH$_2$), 23.8(CH$_2$), 14.1(CH$_3$), 12.1(CH$_3$S).

FAB HRMS Calcd. for C$_{12}$H$_{22}$N$_3$O$_4$S [M+H]$^+$ 304.1331; found 304.1346.

Methyl 3-(4-methoxycarbonyl-1H-[1,2,3]-triazol-1-yl)-3-deoxy-1-thio-β-D-galactopyranoside (10)

Compound 4 (10 mg, 0.023 mmol) was dissolved in methanol (1.5 mL) and stirred over night at room temperature with sodium methoxide solution 1M (0.5 mL). The mixture was neutralized with Duolite™ resin, filtered and concentrated in vacuo. The residue was purified by column chromatography (SiO$_2$, CH$_2$Cl$_2$:MeOH 25:1) to give 10 (5 mg, 70%).

$^1$H NMR (400 MHz, D$_2$O) δ 8.73 (s, 1H, H-5'), 5.03 (dd, 1H, J$_{3,4}$=3.0, J$_{2,3}$=10.7, H-3), 4.65(d, 1H, J$_{1,2}$=9.6, H-1), 4.31 (t, 1H, H-2), 4.22(d, 1H, H-4), 3.98(dd, 1H, H-5), 3.95(s, 3H, CH$_3$O), 3.80(dd, 1H, J$_{6a,6b}$=11.8, J$_{5,6a}$=7.3, H-6a), 3.73(dd, 1H, J$_{5,6b}$=5.0, H-6b), 2.28 (s, 3H, CH$_3$S).

$^{13}$C NMR (100.6 MHz, D$_2$O) δ 162.8(C=O), 139.5(C-4'), 129.0(C-5'), 87.0(C-1), 79.6(C-5), 68.2(C-4), 67.5(C-3), 66.4(C-2), 61.1(C-6), 53.0(CH$_3$O), 11.8(CH$_3$S).

FAB HRMS Calcd. for C$_{11}$H$_{17}$O$_6$N$_3$SNa [M+Na]$^+$ 342.0734; found 342.0723.

Methyl 3-deoxy-3-(4-(1-hydroxy-1-cyclohexyl)-1H-[1,2,3]-triazol-1-yl)-1-thio-β-D-galactopyranoside (11)

Column SiO$_2$, CH$_2$Cl$_2$:MeOH 17:1, yield 6.9 mg, 87%.

$^1$H NMR (300 MHz, MeOD) δ 7.93(s, 1H, H-5'), 4.74(dd, 1H, J$_{2,3}$=10.6, J$_{3,4}$=3.0, H-3), 4.45(d, 1H, J$_{1,2}$=9.4, H-1), 4.18 (dd, 1H, H-2), 4.08(d, 1H, H-4), 3.82-3.53(m, 3H, H-5, 2H-6), 2.25(s, 3H, CH$_3$S), 2.02-1.28(m, 10H, Cyclohexyl).

$^{13}$C NMR (100.6 MHz, MeOD) δ 156.3(C-4'), 121.9(C-5'), 88.7(C-1), 81.0(C-5), 70.4(cyclohexyl), 69.8(C-4), 68.8(C-3), 67.7(C-2), 62.3(C-6), 38.9[2C], 26.6, 23.1[2C] (Cyclohexyl), 12.1(CH$_3$S).

FAB HRMS Calcd. for C$_{15}$H$_{26}$O$_5$N$_3$S [M+H]$^+$ 360.1593; found 360.1596.

Methyl 3-deoxy-3-(4-phenyl-1H-[1,2,3]-triazol-1-yl)-1-thio-β-D-galactopyranoside (12)

Column SiO$_2$, heptane:EtOAc 1:3, yield 6.5 mg, 90%.

$^1$H NMR (400 MHz, MeOD) δ 7.84-7.81(m, 2H, o-Ph), 7.45-7.41(m, 2H, m-Ph), 7.33(tt, 1H, J$_{m,p}$=7.4, J$_{o,p}$=1.2, p-Ph), 4.83(dd, 1H, J$_{3,4}$=3.0, H-3), 4.49(d, 1H, J$_{1,2}$=9.4, H-1), 4.27(dd, 1H, J$_{2,3}$=10.5, H-2), 4.14(d, 1H, H-4), 3.82-3.68(m, 3H, H-5, 2H-6), 2.27(s, 3H, CH$_3$S).

$^{13}$C NMR (100.6 MHz, MeOD) δ 148.3 (C-4'), 131.9, 130.0 [2C], 129.2[2C], 126.6(Ph), 121.8(C-5'), 88.7(C-1), 81.0(C-5), 69.8(C-4), 69.1(C-3), 67.7(C-2), 62.4(C-6), 12.1 (CH$_3$S).

FAB HRMS Calcd. for C$_{15}$H$_{20}$N$_3$O$_4$S [M+H]$^+$ 338.1174; found 338.1179.

Methyl 3-deoxy-3-(4-p-tolylsulfonyl-1H-[1,2,3]-triazol-1-yl)-1-thio-β-D-galactopyranoside (13)

Column SiO$_2$, CH$_2$Cl$_2$:MeOH 17:1, yield 5.8 mg, 75%.

$^1$H NMR (300 MHz, MeOD) δ 8.69(s, 1H, H-5'), 7.91(d, 2H, J$_{H,H}$=8.3, o-Ph), 7.41(d, 2H, J$_{H,H}$=8.0, m-Ph), 4.88(dd, 1H, H-3 partially obscured under H$_2$O peak), 4.43(d, 1H, J$_{1,2}$=9.3, H-1), 4.19(dd, 1H, J$_{2,3}$=10.4, H-2), 4.05(d, 1H, J$_{3,4}$=2.9, H-4), 3.78-3.60(m, 3H, H-5, 2H-6), 2.46, 2.25 (each s, each 3H, 2CH$_3$).

$^{13}$C NMR (100.6 MHz, MeOD) δ 149.6, 146.6, 139.1(C-4', C-1Ph, C-4PH), 131.1, 129.0(each 2C, Ph), 128.0(C-5'), 88.5 (C-1), 80.8(C-5), 69.6(C-3), 69.4(C-4), 67.5(C-2), 62.3(C-6), 21.6(CH$_3$Ph), 11.9 (CH$_3$S)

General Procedure for the Preparation of Amides 14-18

The ester 4 (10 mg, 0.023 mmol) was stirred with the amine (x, 0.25 mL) in water or methanol (1.0 mL) for (t) time and at (T) temperature. The residue obtained after the evaporation of the solvent was purified by column chromatography using the eluent indicated.

Methyl 3-(4-methylaminocarbonyl-1H-[1,2,3]-triazol-1-yl)-3-deoxy-1-thio-β-D-galactopyranoside (14)

x=Methyl amine, t=12 hours, Column SiO$_2$, CH$_2$Cl$_2$: MeOH 15:1, yield: 7.0 mg, 98%.

$^1$H NMR (400 MHz, MeOD) δ 8.43(s, 1H, H-5'), 4.84(dd, 1H, J$_{2,3}$=10.6, J$_{3,4}$=3.0, H-3), 4.46(d, 1H, J$_{1,2}$=9.2, H-1), 4.19 (dd, 1H, H-2), 4.10(d, 1H, H-4), 3.80-3.67(m, 3H, H-5, 2H-6), 2.92(s, 3H, CH$_3$N), 2.25(s, 3H, CH$_3$S).

$^{13}$C NMR (100.6 MHz, MeOD) δ 163.4(C=O), 143.5(C-4'), 126.6(C-5'), 88.6(C-1), 81.0(C-5), 69.6(C-4), 69.1(C-3), 67.7(C-2), 62.4(C-6), 26.1(CH$_3$N), 12.0(CH$_3$S).

FAB HRMS Calcd. for C$_{11}$H$_{18}$N$_4$O$_5$SNa [M+Na]$^+$ 341.0896; found 341.0892.

Methyl 3-(4-butylaminocarbonyl-1H-[1,2,3]-triazol-1'-yl)-3-deoxy-1-thio-β-D-galactopyranoside (15)

x=buthyl amine, t=12 hours, T=r.t., Column SiO$_2$, CH$_2$Cl$_2$: MeOH 25:1, yield: 7.2 mg, 90%.

$^1$H NMR (400 MHz, D$_2$O) δ 8.54(s, 1H, H-5'), 5.01(dd, 1H, J$_{2,3}$=10.7, H-3), 4.65(d, 1H, J$_{1,2}$=9.6, H-1), 4.32(t, 1H, H-2), 4.22(d, 1H, J$_{3,4}$=2.8, H-4), 3.98(dd, 1H, H-5), 3.80(dd, 1H, J$_{6a,6b}$=11.7, J$_{5,6a}$=7.3, H-6a), 3.73(dd, 1H, J$_{5,6b}$=5.0, H-6b), 3.40(t, 2H, J$_{H,H}$=7.0, CH$_2$N), 2.28(s, 3H, CH$_3$S), 1.59(m, 2H, CH$_2$), 1.37(m, 2H, CH$_2$), 0.91(t, 3H, J$_{H,H}$=7.0, CH$_3$).

$^{13}$C NMR (100.6 MHz, D$_2$O) δ 162.3(C=O), 142.5(C-4'), 126.4(C-5'), 87.0(C-1), 79.7(C-5), 68.3(C-4), 67.4(C-3), 66.4(C-2), 61.1(C-6), 39.5(CH$_2$N), 30.9(CH$_2$), 19.8(CH$_2$), 13.3(CH$_3$CH$_2$), 11.8(CH$_3$S).

FAB HRMS Calcd. for C$_{14}$H$_{25}$N$_4$O$_5$S [M+H]$^+$ 361.1546; found 361.1542.

Methyl 3-(4-benzylaminocarbonyl-1H-[1,2,3]-triazol-1-yl)-3-deoxy-1-thio-β-D-galactopyranoside (16)

x=Benzyl amine, t=three days, T=r.t., Column SiO$_2$, CH$_2$Cl$_2$:MeOH 25:1, yield: 7.0 mg, 80%

$^1$H NMR (400 MHz, D$_2$O) δ 8.58(s, 1H, H-5'), 7.41-7.35 (m, 5H, Ph), 5.02(dd, 1H, J$_{2,3}$=10.7, H-3), 4.65(d, 1H, J$_{1,2}$=9.6, H-1), 4.62(s, 2H, CH$_2$), 4.32(t, 1H, H-2), 4.23(d, 1H, $J_{3,4}$=2.8, H-4), 3.98(dd, 1H, H-5), 3.80(dd, 1H, $J_{5,6a}$=7.4, $J_{6a,6b}$=11.7, H-6a), 3.73(dd, 1H, $J_{5,6b}$=5.0, H-6b), 2.28(s, 3H, CH$_3$S).

$^{13}$C NMR (100.6 MHz, D$_2$O) δ 162.4(C=O), 142.4(C-4'), 138.1, 129.2[2C], 127.9, 127.6[2C] (Ph), 126.6(C-5'), 87.0 (C-1), 79.7(C-5), 68.3(C-4), 67.4(C-3), 66.4(C-2), 61.1(C-6), 43.2(CH$_2$Ph), 11.8(CH$_3$S).

FAB HRMS Calcd. for C$_{17}$H$_{22}$N$_4$O$_5$SNa [M+Na]$^+$ 417.1209; found 417.1224.

Methyl 3-{4-(3-hydroxyprop-1-ylaminocarbonyl)-1H-[1,2,3]-triazol-1-yl}-3-deoxy-1-thio-β-D-galactopyranoside (17)

x=3-aminopropanol, t=two days, T=45° C., Column SiO$_2$, CH$_2$Cl$_2$:MeOH 10:1, yield: 7.0 mg, 86%

$^1$H NMR (400 MHz, D$_2$O) δ 8.56(s, 1H, H-5'), 5.01(dd, 1H, $J_{3,4}$=3.0, $J_{2,3}$=10.6, H-3), 4.65(d, 1H, $J_{1,2}$=9.6, H-1), 4.32(t, 1H, H-2), 4.22(d, 1H, H-4), 3.98(dd, 1H, H-5), 3.80(dd, 1H, $J_{5,6a}$=7.4, $J_{6a,6b}$=11.8, H-6a), 3.73(dd, 1H, $J_{5,6b}$=5.0, H-6b), 3.69(t, 2H, $J_{H,H}$=6.4, CH$_2$O), 3.49(t, 2H, $J_{H,H}$=6.9, CH$_2$N), 2.28(s, 3H, CH$_3$S), 1.87(m, 2H, CH$_2$).

$^{13}$C NMR (100.6 MHz, D$_2$O) δ 162.4(C=O), 142.5(C-4'), 126.4(C-5'), 87.0(C-1), 79.7(C-5), 68.3(C-4), 67.4(C-3), 66.4(C-2), 61.1(C-6), 59.6(CH$_2$O), 36.7(CH$_2$N), 31.3(CH$_2$), 11.8(CH$_3$S).

FAB HRMS Calcd. for C$_{13}$H$_{22}$N$_4$O$_6$SNa [M+Na]$^+$ 385.1158; found 385.1180.

Methyl 3-{4-[2-(N-morpholino)-ethylaminocarbonyl]-1H-[1,2,3]-triazol-1-yl}-3-deoxy-1-thio-β-D-galactopyranoside (18)

x=N-morpholinoethylamine, t=four days, T=45° C., Column SiO$_2$, CH$_2$Cl$_2$:MeOH 17:1, yield: 7.0 mg, 75%.

$^1$H NMR (400 MHz, MeOD) δ 8.44(s, 1H, H-5'), 4.85 (obscured under H$_2$O peak, 1H, H-3), 4.46(d, 1H, $J_{1,2}$=9.2, H-1), 4.19(dd, 1H, $J_{2,3}$=10.4, H-2), 4.09(d, 1H, $J_{3,4}$=2.9, H-4), 3.80-3.66(m, 7H, H-5, 2H-6, 2 (CH$_2$O)), 3.55 (t, 2H, $J_{H,H}$=6.6, CH$_2$NC=O), 2.59 (t, 2H, $J_{H,H}$=6.6, CH$_2$N), 2.53 (bt, 4H, 2(CH$_2$N), 2-0.25(s, 3H, CH$_3$S).

$^{13}$C NMR (100.6 MHz, MeOD) δ 162.7(C=O), 143.5(C-4'), 126.7(C-5'), 88.6 (C-1), 80.9 (C-5), 69.6 (C-4), 69.1 (C-3), 67.8 ((CH$_2$)$_2$O), 67.7 (C-2), 62.3 (C-6), 58.5 (CH$_2$N), 54.7 ((CH$_2$)$_2$N), 36.9 (CH$_2$NC=O), 12.0 (CH$_3$S).

FAB HRMS Calcd. for C$_{16}$H$_{27}$N$_5$O$_6$SNa [M+Na]$^+$ 440.1580; found 440.1579.

Methyl 2,4,6-tri-O-acetyl-3-deoxy-3-(4-methoxycarbonyl-1H-[1,2,3]-triazol-1-yl)-β-D-galactopyranosyl-(1-4)-2-acetamido-3,6-di-O-acetyl-2-deoxy-β-D-glucopyranoside (20)

A mixture of methyl 2,4,6-tri-O-acetyl-3-azido-3-deoxy-β-D-galactopyranosyl (1→4)-2-acetamido-3,6-di-O-acetyl-2-deoxy-β-D-glucopyranoside 19 (prepared by straight-forward O-acetylation of the known methyl 2,4,6-tri-O-acetyl-3-azido-3-deoxy-β-D-galactopyranosyl (1→4)-2-acetamido-6-O-acetyl-2-deoxy-β-D-glucopyranoside; Sörme et al., 2002) (10 mg, 0.028 mmol), the acetylene derivative (1 eq.), copper iodide (0.5 mg, 0.1 eq.), diisopropylethylamine (1 eq.) and toluene (1 mL) were stirred for 24 h at 45°. The solvent was evaporated and the product was purified by column chromatography (SiO$_2$, Toluene:Acetone 2:1) to give 20 (10.1 mg, 90%).

$^1$H NMR (400 MHz, CDCl$_3$) δ 8.14(s, 1H, H-5"), 5.64(d, 1H, $J_{2,NH}$=9.4, NH), 5.55(dd, 1H, $J_{2',3'}$=11.5, H-2'), 5.49(d, 1H, $J_{3',4'}$=3.2, H-4'), 5.16(dd, 1H, H-3'), 5.12(dd, 1H, $J_{2,3}$=9.7, H-3), 4.68(d, 1H, $J_{1',2'}$=7.6, H-1'), 4.49(dd, 1H, $J_{5,6a}$=2.6, $J_{H,H}$=11.9, H-6a), 4.40(d, 1H, $J_{1,2}$=7.7, H-1), 4.16 (dd, 1H, $J_{5,6b}$=5.4, H-6b), 4.10(s, 3H, H-5', 2H-6'), 4.03(dt, 1H, H-2), 3.93(s, 3H, CH$_3$O), 3.83(t, 1H, J=8.7, H-4), 3.65 (ddd, 1H, H-5), 3.46(s, 3H, CH$_3$O), 2.14(s, 3H, CH$_3$), 2.08(s, 6H, 2CH$_3$), 2.05, 1.98, 1.89(each s, each 3H, 3CH$_3$C=O).

$^{13}$C NMR (100.6 MHz, CDCl$_3$) δ 170.6, 170.3, 170.2, 170.1, 169.0, 168.7, 160.5 (7C=O), 140.1(C-4"), 126.7(C-5"), 101.7(C-1), 101.0(C-1'), 75.7(C-4'), 72.5(C-5), 72.1(C-3), 71.7(C-5'), 67.8[2C](C-2', C-4'), 62.1(C-3'), 62.0(C-6), 60.7(C-6'), 56.6(CH$_3$O), 53.2(C-2), 52.2(CH$_3$O), 23.2, 20.7 [2C], 20.5, 320.2, 20.1(6CH$_3$).

FAB HRMS Calcd. for C$_{29}$H$_{41}$N$_4$O$_{17}$ [M+H]$^+$ 717.2467; found 717.2457.

Methyl 3-(4-methylaminocarbonyl-1H-[1,2,3]-triazol-1-yl)-3-deoxy-β-D-galactopyranosyl-(1→4)-2-acetamido-2-deoxy-β-D-glucopyranoside (21)

Compound 20 (10 mg) was dissolved in methylamine (40% in water, 2 mL), stirred for 12 h, concentrated, and purified by column chromatography. (SiO$_2$, CH$_2$Cl$_2$:MeOH 5:1) to give 21 (5.6 mg, 80%).

$^1$H NMR (400 MHz, D$_2$O) δ 8.55(s, 1H, H-5"), 5.01(dd, 1H, $J_{3',4'}$=2.9, $J_{2',3'}$=11.2, H-3'), 4.74(d, 1H, $J_{1',2'}$=7.6, H-1'), 4.67(d, 1H, $J_{1,2}$=7.8, H-1), 4.24(dd, 1H, H-2'), 4.17(d, 1H, H-4'), 4.00(m, 2H, H-5', H-6a), 3.87-3.72(m, 6H, H-2, 2H-6', H-3, H-4, H-6b), 3.61(m, 1H, H-5), 3.50(s, 3H, CH$_3$O), 2.94 (s, 3H, CH$_3$N), 2.04(s, 3H, CH$_3$C=O).

$^{13}$C NMR (100.6 MHz, D$_2$O) δ 175.1, 162.9(2C=O), 142.4(C-4"), 126.3(C-5"), 103.4(C-1'), 102.2(C-1), 76.4(C-5'), 75.1(C-5), 68.2(C-2'), 68.0(C-4'), 66.0(C-3'), 60.3(C-6), 57.5(CH$_3$O), 55.4(C-6'), 78.8, 72.9, 61.1(C-2, C-3, C-4), 26.0 (CH$_3$N), 22.5(CH$_3$C=O).

FAB HRMS Calcd. for C$_{19}$H$_{32}$N$_5$O$_{11}$ [M+H]$^+$ 506.2099; found 506.2101.

1,2,4,6-Tetra-O-acetyl-3-deoxy-3-[4-(methoxycarbonyl)-1H-[1,2,3]-triazol-1-yl]-D-galactopyranose 23

A mixture of 1,2,4,6-tetra-O-acetyl-3-azido-3-deoxy-D-galactopyranose 22 (Lowary and Hindsgaul, 1994) (10 mg, 0.027 mmol), methyl propiolate (2.4 μL, 1 eq.), copper iodide (0.6 mg, 0.1 eq.), diisopropylethylamine (1 eq.), and toluene (1 mL) were stirred together for 12 h at r.t. The solvent was evaporated and the product was purified by column chromatography (SiO$_2$, heptane:EtOAc 2:1) to give 23 (12.2 mg, 93%).

$^1$H NMR (300 MHz, CDCl$_3$) δ 8.16 (s, 1H, H-5'A), 8.10 (s, 1H, H-5'B), 6.50 (d, 1H, $J_{1,2}$=3.5, H-1A), 5.92 (dd, 1H, $J_{2,3}$=11.8, H-2A), 5.83 (m, 2H, H-1B, H-2B), 5.59 (d, 1H, H-4A), 5.54 (d, 1H, H-4B), 5.40 (dd, 1H, $J_{3,4}$=3.0, H-3A), 5.22 (dd, 1H, $J_{2,3}$=11.0, $J_{3,4}$=3.3, H3-B), 4.50 (t, 1H, J=6.5, H-5A), 4.25-4.07 (m, 5H, H-5B, 2H-6B, 2H6A), 3.95(s, 6H, CH$_3$OA, CH$_3$OB), 2.21, 2.16, 2.15, 2.12, 2.09, 2.08, 1.88, 1.87 (each s, each 3H, 8CH$_3$), 2.04 (s, 6H, 2CH$_3$).

$^{13}$C NMR (100.6 MHz, CDCl$_3$) δ 170.2, 170.1, 169.3, 169.0, 168.9, 168.7, 168.6, 168.5, 160.6, 160.5(10 C=O), 140.2, 140.1(C-4'A, C-4'B), 126.6(C-5'A, C-5'B), 92.4(C-1B), 88.9(C-1A), 72.7(C-5B), 68.9(C-5A), 68.1(C-4A), 67.9 (C-4B), 66.5(C-2B), 65.2(C-2A), 62.2(C-3B), 61.0, 60.8(C-6A, C-6B), 58.2(C-3A), 52.3(CH$_3$OA, CH$_3$OB), 20.7, 20.6, 20.5[2C], 20.2[2C], 20.1, 20.0(8 CH$_3$).

2,4,6-Tri-O-acetyl-3-deoxy-3-[4-(methoxycarbonyl)-1H-1,2,3-triazol-1-yl]-α-D-galactopyranosyl bromide (24)

1,2,4,6-Tetra-O-acetyl-3-deoxy-3-[4-(methoxycarbonyl)-1H-1,2,3-triazol-1-yl]-D-galactopyranose 23 (33 mg, 0.072 mmol) was dissolved in dichloromethane (1 ml) which had been dried over 4 Å molecular sieves. Acetic anhydride (14 l, 0.20 mmol) and HBr (0.2 ml of a 33% solution in AcOH) were added, and the mixture was stirred under $N_2$ at room temperature. After 3 h 15 min, the reaction mixture was diluted with dichloromethane (30 ml) and poured into ice-water (30 ml). The organic phase was washed with $NaHCO_3$ (30 ml of a saturated aqueous solution), dried ($MgSO_4$), filtered and concentrated in vacuo. The residue was purified by flash column chromatography to give 24 (16 mg, 46%), which was used immediately in the synthesis of 25.

Bis-[2,4,6-tri-O-acetyl-3-deoxy-3-(4-(methoxycarbonyl)-1H-1,2,3-triazol-1-yl)-β-D-galactopyranosyl] sulfane (25)

Sodium sulfide nonahydrate (42 mg, 0.14 mmol) was dried in air using a heat gun and then allowed to cool under vacuum. Molecular sieves 4 Å (ca. 20 mg) were added. Compound 24 (16 mg, 0.033 mmol) was dissolved in distilled acetonitrile (1 ml) and added to the reaction vessel. The mixture was stirred at room temperature for 7 h 30 min. After this time, TLC (heptane:EtOAc 1:3) indicated the complete consumption of starting material ($R_f$ 0.7) and the presence of a major product ($R_f$ 0.2). The reaction mixture was diluted with ethyl acetate (30 ml) and poured into $H_2SO_4$ (30 ml of a 10% aqueous solution). The organic phase was dried ($MgSO_4$), filtered and concentrated in vacuo. The residue was purified by flash column chromatography ($SiO_2$, heptane:EtOAc 1:4) to give 25 (8 mg, 58%).

Bis-(3-deoxy-3-{4-[(methylamino)carbonyl]-1H-1,2,3-triazol-1-yl}-β-D-galactopyranosyl)sulfane (26)

Compound 25 (11 mg, 0.012 mmol) was suspended in a methylamine solution (40% in water, 2 ml). The mixture was stirred at room temperature for 6 h. After this time, the mixture was concentrated in vacuo. The residue was purified by HPLC (reversed phase C18, gradient $H_2O \rightarrow MeCN$) to give 26 (3.5 mg, 62%). White solid;
$^1H$ NMR (300 MHz, $D_2O$) δ 2.93 (6H, s, $NHCH_3$), 3.72 (2H, dd, $J_{5,6}$ 4.4 Hz, $J_{6,6'}$ 11.9 Hz, H-6), 3.81 (2H, dd, $J_{5,6'}$ 7.4 Hz, H-6'), 4.01 (2H, dd, H-5), 4.21 (2H, d, $J_{3,4}$ 2.6 Hz, H-4), 4.38 (2H, at, J 10.2 Hz, H-2), 5.03 (2H, dd, $J_{2,3}$ 10.7 Hz, H-3), 5.11 (2H, d, $J_{1,2}$ 9.8 Hz, H-1), 8.55 (2H, s, triazole-H);
FAB HRMS Calcd. for $C_{20}H_{31}N_8O_{10}S$ $[M+H]^+$ 575.1884; found 575.1887.

Evaluation of 8-18, 21, and 26 as Inhibitors of Galectin-3 by Use of Fluorescense Polarization Compounds 8-18, 21, and 26, together with the known reference compounds 27, 28, and 29, were evaluated for their efficiency in inhibiting galectin-3 in a known fluorescence polarization-based assay (Sörme et al., 2003a, 2004). To 100 µL of galectin-3 (1 µM) and a fluorescent probe (2-(fluorescein-5/6-yl-carbonyl)-aminoethyl 4-O-[3-O-(4-methoxy]benzyl)-β-D-galactopyranosyl]-β-D-glucopyranoside, 0.1 µM) were added inhibitor solution (3.2-10000 µM, 100 µL), the plate was incubated under slow rotary shaking in the dark for 5 minutes, and fluorescence polarization measured at room temperature. The fluorescence was measured from above in 96 well microtiter plates (black polystyrene, Costar, Corning, N.Y.) using a PolarStar instrument (BMG, Offenburg; Germany). Control wells containing only fluorescent probe or fluorescein were included. All dilutions and measurements were done in PBS.

Examples of in vivo Efficacy of Galectin Inhibition in Inflammation and Cancer.

Inflammation

As mentioned above, many studies suggest a role for galectin-3 in enhancement of the inflammatory response. For example, the addition of galectin-3 to neutrophil leukocytes from an inflammatory site, or primed by exposure to LPS, results in increased generation of toxic oxygen radicals. Lactose can inhibit this response (Karlsson et al., 1998; Almquist et al., 2001). In another study (Sano et al., 2000), galectin-3 was found to be chemotactic to macrophages and monocytes, both in vitro and in vivo. Either lactose or the isolated CRD of galectin-3 (galectin 3C), able to bind the same saccharide receptor as galectin-3 but not cross link it (see below), acted as inhibitors of this response. The substances described in the present invention would be much more effective as inhibitors of the above mentioned responses than lactose because they are much more potent galectin-3 inhibitors. They would also be much more useful in vivo than lactose and the galectin-3C because they are small molecules, more hydrophobic and probably more stable to degradation.

Cancer

As mentioned above, several studies of models of human cancer in mice indicate that enhanced expression of galectin-3 results in faster tumor growth and more metastasis (Bresalier et al., 1998; reviewed by Leffler, 2001 and Takenaka et al in Leffler (editor), 2004b). Injection of a saccharide with inhibitory potency to galectin-3, but perhaps also other proteins, was reported to diminish prostate cancer in rat (Pienta et al., 1995). Hence, potent small-molecule inhibitors of galectin-3 are expected to have similar anticancer effects as galectin-3C (John et al., 2003).

REFERENCES

Ahmad, N., Gabius, H. J., Andre, S., Kaltner, H., Sabesan, S., Roy, R., Liu, B., Macaluso, F., and Brewer, C. F. (2004) Galectin-3 precipitates as a pentamer with synthetic multivalent carbohydrates and forms heterogeneous cross-linked complexes. *J. Biol. Chem.* 279: 10841-10847.

Almkvist, J., Faldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832-837.

André, S., Ortega, P. J. C., Perez, M. A., Roy, R., and Gabius, H.-J. (1999) Lactose-containing starburst dendrimers: influence of dendrimer generation and binding-site orientation of receptors (plant/animal lectins and immunoglobulins) on binding properties. *Glycobiology* 11:1253-1262.

André, S., Kaltner, H., Furuike, T., Nishimura, S.-I., and Gabius, H.-J. (2004) Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets. *Bioconj. Chem.* 15:87-98.

Arnusch, C. J., André, S., Valentini, P., Lensch, M., Russwurm, R., Siebert, H.-C., Fischer, M. J. E., Gabius, H.-J., and Pieters, R. J. (2004) Interference of the galactosedependent binding of lectins by novel pentapeptide ligands. *Bioorg. Med. Chem. Lett.* 14:1437-1440.

Barondes, S. H., Cooper, D. N. W., Gitt, M. A., and Leffler, H. (1994). Galectins. Structure and function of a large family of animal lectins. *J. Biol. Chem.* 269:20807-20810.

Bresalier, R. S., Mazurek, N., Sternberg, L. R., Byrd, J. C., Yunker, C. K., Nangia-Makker, P., Raz, A. (1998) Metastasis of human colon cancer is altered by modifying expression of the beta-galactoside-binding protein galectin 3. *Gastroenterology* 115:287-296.

Brewer, C. F., Miceli, M. C., and Baum, L. G. (2002) Clusters, bundles, arrays and lattices: novel mechanisms for lectin-saccharide-mediated cellular interactions. *Curr. Opin. Struct. Biol.* 12: 616-623.

David, A., Kopecková, P., Minko, T., Rubinstein, A., and Kopecek, J. (2004) Design of a multivalent galactoside ligand for selective targeting of HPMA copolymer-doxorubicin conjugates to human colon cancer cells. *Eur. J. Cancer* 40: 148-157.

Glinsky, G. V., Price, J. E., Glinsky, V. V., Mossine, V. V., Kiriakova, G., Metcalf, J. B. (1996) Inhibition of human breast cancer metastasis in nude mice by synthetic glycoamines. *Cancer Res.* 56:5319-5324.

Houzelstein, D., Goncalves, I. R., Fadden, A. J., Sidhu, S. S., Cooper, D. N., Drickamer, K., Leffler, H., and Poirier, F. (2004) Phylogenetic Analysis of the Vertebrate Galectin Family. *Mol. Biol. Evol.* ????.

Hsu, D. K., Yang, R. Y., Pan, Z., Yu, L., Salomon, D. R., Fung-Leung, W. P., Liu, F. T. (2000) Targeted disruption of the galectin-3 gene results in attenuated peritoneal inflammatory responses. *Am. J. Pathol.* 156:1073-1083.

Huflejt M E, Mossine V V, Naidenko O, Jazayeri M, Rogers P, Tinari N, Iacobelli S, Elliot, M., Lustgarten J and Croft, M. (2001) Synthetic lactulose amines bind tumor-promoting galectins-1 and -4, and inhibit breast cancers in Her-2/neu transgenic mice, 24th Annual San Antonio Breast Cancer Symposium, abstract.

Huflejt, M. E. and Leffler, H. (2004) Galectin-4 in normal tissues and cancer. *Glycoconj. J.* 20: 247-255.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9:2374-2383.

Karima, R., Matsumoto, S., Higahsi, H., Matsushima, K. (1999) The molecular pathogenesis of Endotoxic Shock and Organ Failure. *Molecular Medicine Today* 5:123-132.

Karlsson, A., Follin, P, Leffler, H., Dahlgren, C. (1998) Galectin-3 activates the NADPH-oxidase in exudated but not peripheral blood neutrophils. *Blood* 91:3430-3438.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lobsanov, Y. D. and Rini, J. M. (1997) Galectin Structure. *Trends. Glycosci. Glycotech.* 45:145-154.

Lowary, T. L. and Hindsgaul, O. (1994) Recognition of synthetic O-methyl, epimeric, and amino analogues of the acceptor α-L-Fucp-(1-2)-β-D-Galp-OR by the blood-group A and B gene-specified glycosyltransferases. *Carbohydr. Res.* 251:33-67.

Massa, S. M., Cooper, D. N. W., Leffler, H., Barondes, S. H. (1993) L-29, an endogenous lectin, binds to glycoconjugate ligands with positive cooperativity. *Biochemistry* 32; 260-267.

Naidenko, O., Kronenberg, M., Glinsky, G., and Huflejt, M. E. (2000) Interaction of galectins with low molecular weight lactosylaminoconjugates. *Glycobiology* 10:abstract 60.

Nangia-Makker, P., Hogan, V., Honjo, Y., Baccarini, S., Tait, L., Bresalier, R., and Raz, A. (2002) Inhibition of human cancer cell growth and metastasis in nude mice by oral intake of modified citrus pectin, *J. Natl. Cancer Inst.* 94:1854-1862.

Pienta, K. J., Naik, H., Akhtar, A., Yamazaki, K., Replogle, T. S., Lehr, J., Donat, T. L., Tait, L., Hogan, V., Raz, A. (1995) Inhibition of spontaneous metastasis in a rat prostate cancer model by oral administration of modified citrus pectin. *J. Natl. Cancer Inst.* 87:348-353

Platt, D. and Raz, A. (1992) *J. Natl. Cancer. Inst.* 84: 438-442.

Pohl, N. L. and Kiessling, L. L. (1999) Scope of multivalent ligand function: Lactose-bearing neoglycopolymers by ring-opening metathesis polymerization. *Synthesis* 1515-1519.

Poirier, F. (2002) Roles of galectins in vivo. *Biochem. Soc. Symp.* 69: 95-103.

Rubinstein, N., Alvarez, M., Zwirner, N. W., Toscano, M. A., Ilarregui, J. M., Bravo, A., Mordoh, J., Fainboim, L., Podhajcer, O. L., and Rabinovich, G. A. (2004) Targeted inhibition of galectin-1 gene expression in tumor cells results in heightened T cell-mediated rejection; A potential mechanism of tumor-immune privilege. *Cancer Cell* 5: 241-251.

Sano, H., Hsu, D. K., Yu, L., Apgar, J. R., Kuwabara, I., Yamanaka, T., Hirashima, M., Liu, F. T. (2000) Human galectin-3 is a novel chemoattractant for monocytes and macrophages. *J. Immunol.* 165:2156-2164.

Seetharaman, J., Kanigsberg, A., Slaaby, R., Leffler, H., Barondes, S. H., Rini, J. M. (1998) X-ray crystal structure of the human galectin-3 carbohydrate recognition domain at 2.1-Å resolution. *J. Biol. Chem.* 273:13047-13052.

Sörme, P., Qian, Y., Nyholm, P.-G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* accepted for publication.

Tornøe, C. W., Christensen, C., and Meldal, M. (2002) Peptidotriazoles on solid phase: [1,2,3]-Triazoles by regiospecific copper(I)-catalyzed 1,3-dipolar cycloaddition of terminal alkynes to azides. *J. Org. Chem.* 67: 3057-3064.

Trahey, M. and Weissman, I. L. (1999) Cyclophilin C-associated protein: a normal secreted glycoprotein that down-modulates endotoxin and proinflammatory responses in vivo. *Proc. Natl. Acad. Sci. USA* 96:3006-3011.

Vrasidas, I., André, S., Valentini, P., Böck, C., Lensch, M., Kaltner, H., Liskamp, R. M. J., Gabius, H.-J., and Pieters, R. J. (2003) Rigidified multivalent lactose molecules and their interactions with mammalian galectins: a route to selective inhibitors. *Org. Biomol. Chem.* 1: 803-810.

The invention claimed is:

1. A compound of the general formula (I):

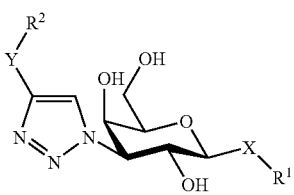

wherein
the configuration of the pyranose ring is D-galacto;
X is selected from the group consisting of O and S;
Y is selected from the group consisting of $CH_2$, CO, $SO_2$, and phenyl, or is a bond;
$R^1$ is selected from the group consisting of:
a) D-galactose;
b) C3-substituted D-galactose;
c) C3-[1,2,3]-triazol-1-yl-substituted D-galactose;
d) hydrogen, an alkyl group, an alkenyl group and an aryl group; and
e) an imino group and a substituted imino group;
$R^2$ is selected from the group consisting of an amino group, a substituted amino group, an alkyl group, a substituted alkyl group, an alkoxy group, a substituted alkoxy group, an alkylamino group, a substituted alkylamino group, substituted naphthyl group, a thienyl group, and a substituted thienyl group;
wherein said substituent is one or more selected from the group consisting of halogen, alkoxy, alkyl, nitro, sulfo, amino, hydroxy or carbonyl group.

2. A compound according to claim 1, wherein Y is CO, $SO_2$, or a bond.

3. A compound according to claim 1, wherein $R^2$ is an amine or an aryl group.

4. A compound according to claim 1, wherein $R^2$ is a substituted amine or a substituted aryl group; wherein the substituent is one or more selected from the group consisting of halogen, alkoxy, alkyl, nitro, sulfo, amino, hydroxy or carbonyl group.

5. A compound according to claim 1, wherein $R^1$ is galactose glucose or N-acetylglucosamine.

6. A compound according to claim 1, wherein $R^1$ is a C3-[1,2,3]-triazol-1-yl-substituted galactose.

7. A compound according to claim 1, wherein X is S.

8. A compound according to claim 1, wherein said compound is methyl 3-deoxy-3-(1H-[1,2,3]-triazol-1-yl)-1-thio-β-D-galactopyranoside (8).

9. A compound according to claim 1, for use as a medicament.

10. A pharmaceutical composition comprising a compound according to claim 1 as active ingredient together with a pharmaceutically acceptable adjuvant, diluent, excipient or carrier.

11. A pharmaceutical composition according to claim 10, comprising from 1 to 99 weight % of a pharmaceutically acceptable adjuvant, diluent, excepient or carrier and from 1 to 99 weight % of a compound according to claim 1.

12. The compound of claim 1, wherein said substituted phenyl group is selected from the group consisting of a halogenated phenyl group, an alkoxylated phenyl group, an alkylated phenyl group, and a trifluoromethylated phenyl group.

13. The compound of claim 12, wherein said halogenated phenyl group is selected from the group consisting of a fluorinated phenyl group, a chlorinated phenyl group, and a brominated phenyl group.

14. A compound according to claim 1, wherein said compound is bis-(3-deoxy-3-(4-(methylaminocarbonyl)-1H-[1,2,3]-triazol-1-yl)-β-D-galactopyranosyl)sulfane (26), methyl 3-deoxy-3-{4-(2-fluorophenyl)-1H-[1,2,3]-triazol-1-yl}-1-thio-β-D-galactopyranoside, methyl 3-deoxy-3-{4-(2-methoxyphenyl)-1H-[1,2,3]-triazol-1-yl}-1-thio-β-D-galactopyranoside, methyl 3-deoxy-3-{4-(3-methoxyphenyl)-1H-[1,2,3]-triazol-1-yl}-1-thio-β-D-galactopyranoside, methyl 3-deoxy-3-{4-(4-methoxyphenyl)-1H-[1,2,3]-triazol-1-yl}-1-thio-β-D-galactopyranoside, methyl 3-deoxy-3-{4-(3,5-dimethoxyphenyl)-1H-[1,2,3]-triazol-1-yl}-1-thio-β-D-galactopyranoside, methyl 3-deoxy-3-{4-(1-naphthyl)-1H-[1,2,3]-triazol-1-yl}-1-thio-β-D-galactopyranoside, methyl 3-deoxy-3-{4-(2-naphthyl)-1H-[1,2,3]-triazol-1-yl}-1-thio-β-D-galactopyranoside, methyl 3-deoxy-3-{4-(2-pyridyl)-1H-[1,2,3]-triazol-1-yl}-1-thio-β-D-galactopyranoside, methyl 3-deoxy-3-{4-(3-pyridyl)-1H-[1,2,3]-triazol-1-yl}-1-thio-β-D-galactopyranoside, methyl 3-deoxy-3-{4-(4-pyridyl)-1H-[1,2,3]-triazol-1-yl}-1-thio-β-D-galactopyranoside, O-{3-deoxy-3-[4-phenyl-[1H-[1,2,3]-triazol-1-yl]-β-D-galactopyranosyl}-3-indol-carbaldoxim, O-{3-deoxy-3-[4-(methylaminocarbonyl)-1H-[1,2,3[-triazol-1-yl]-β-D-galactopyranosyl}-3-indol carbaldoxim, O-{3-deoxy-3-[4-phenyl-[1H-[1,2,3]-triazol-1-yl]-β-D-galactopyranosyl}-(2-hydroxy-5-nitro-phenyl)-carbaldoxim, O-{3-deoxy-3-[4-(methylaminocarbonyl)-1H-[1,2,3]-triazol-1-yl]-β-D-galactopyranosyl}-(2-hydroxy-5-nitro-phenyl)-carbaldoxim, O-{3-deoxy-3-[4-phenyl-[1H -[1,2,3]-triazol-1-yl]-β-D-galactopyranosyl}-(2,5-dihydroxyphenyl)-carbaldoxim, O-{3-deoxy-3-[4-(methylaminocarbonyl)-1H-[1,2,3]-triazol-1-yl]-β-D-galactopyranosyl}-(2,5-dihydroxyphenyl)-carbaldoxim, O-{3-deoxy-3-[4-phenyl-[1H-[1,2,3]-triazol-1-yl]-β-D -galactopyranosyl}-1-naphthyl-carbaldoxim, or O-{3-deoxy-3-[4-(methylaminocarbonyl) -1H-[1,2,3]-triazol-1-yl]-β-D-galactopyranosyl}-1-naphthyl-carbaldoxim.

* * * * *

UNITED STATES PATENT AND TRADEMARK OFFICE
CERTIFICATE OF CORRECTION

PATENT NO. : 7,700,763 B2
APPLICATION NO. : 11/561465
DATED : April 20, 2010
INVENTOR(S) : Leffler et al.

Page 1 of 1

It is certified that error appears in the above-identified patent and that said Letters Patent is hereby corrected as shown below:

In the Claims

Column 29, Line 7-39, Claim 1 should read as follows:

1. A compound of the general formula (1):

wherein
the configuration of the pyranose ring is D-galacto;
X is selected from the group consisting of O and S;
Y is selected from the group consisting of CH2, CO, SO2, and phenyl, or is a bond;
R1 is selected from the group consisting of;
a) D-galactose;
b) C3-substituted D-galactose;
c) C3-[ 1 ,2,3]-triazol-l-yl-substituted D-galactose;
d) hydrogen, an alkyl group, an alkenyl group and an aryl group; and
e) an imino group and a substituted imino group;
R2 is selected from the group consisting of an amino group, a substituted amino group, an alkyl group, a substituted alkyl group, an alkoxy group, a substituted alkoxy group, an alkylamino group, a substituted alkylamino group, a phenyl group, a substituted phenyl, a naphthyl group, a substituted naphthyl group, a thienyl group and a substituted thienyl group
wherein said substituent is one or more selected from the group consisting of halogen, alkoxy, alkyl, nitro, sulfo, amino, hydroxy or carbonyl group.

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 7,700,763 B2 | Page 1 of 2 |
| APPLICATION NO. | : 11/561465 | |
| DATED | : April 20, 2010 | |
| INVENTOR(S) | : Leffler et al. | |

It is certified that error appears in the above-identified patent and that said Letters Patent is hereby corrected as shown below:

In the Claims

Column 29, Line 7-39, Claim 1 should read as follows:

1. A compound of the general formula (1):

wherein
the configuration of the pyranose ring is D-galacto;
X is selected from the group consisting of O and S;
Y is selected from the group consisting of CH2, CO, SO2, and phenyl, or is a bond;
R1 is selected from the group consisting of;
a) D-galactose;
b) C3-substituted D-galactose;
c) C3-[ 1 ,2,3]-triazol-l-yl-substituted D-galactose;
d) hydrogen, an alkyl group, an alkenyl group and an aryl group; and
e) an imino group and a substituted imino group;
R2 is selected from the group consisting of an amino group, a substituted amino group, an alkyl group, a substituted alkyl group, an alkoxy group, a substituted alkoxy group, an alkylamino group, a substituted alkylamino group, a phenyl group, a substituted phenyl, a naphthyl group, a substituted naphthyl group, a thienyl group and a substituted thienyl group
wherein said substituent is one or more selected from the group consisting of halogen, alkoxy, alkyl, nitro, sulfo, amino, hydroxy or carbonyl group.

This certificate supersedes the Certificate of Correction issued February 18, 2014.

Signed and Sealed this
Fifteenth Day of July, 2014

Michelle K. Lee
*Deputy Director of the United States Patent and Trademark Office*

CERTIFICATE OF CORRECTION (continued)

U.S. Pat. No. 7,700,763 B2

In column 29, line 42, cancel the text beginning with "3. A compound according to claim 1, wherein R2 is an" to and ending with "carbonyl group" in column 29, line 48 and insert the following claims:

--3. A compound according to claim 1, wherein R2 is an amine or an aryl group, wherein the aryl group is a phenyl, or naphthyl group.

4. A compound according to claim 1, wherein R2 is a substituted amine or a substituted aryl group wherein the substituted aryl group is a substituted phenyl, or substituted naphthyl group; wherein the substituent is one or more selected from the group consisting of halogen, alkoxy, alkyl, nitro, sulfo, amino, hydroxy or carbonyl group.--